(12) United States Patent
Winston et al.

(10) Patent No.: US 11,918,565 B1
(45) Date of Patent: Mar. 5, 2024

(54) TREATMENT OF POST-OPERATIVE PAIN VIA SCIATIC NERVE BLOCK WITH SUSTAINED-RELEASE LIPOSOMAL ANESTHETIC COMPOSITIONS

(71) Applicant: Pacira Pharmaceuticals, Inc., Parsippany, NJ (US)

(72) Inventors: Roy Winston, Parsippany, NJ (US); Mary DiGiorgi, Parsippany, NJ (US)

(73) Assignee: Pacira Pharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 18/104,970

(22) Filed: Feb. 2, 2023

Related U.S. Application Data

(60) Provisional application No. 63/422,182, filed on Nov. 3, 2022.

(51) Int. Cl.
*A61K 31/44* (2006.01)
*A61K 9/00* (2006.01)
*A61K 9/48* (2006.01)
*A61K 31/661* (2006.01)
*A61K 47/54* (2017.01)

(52) U.S. Cl.
CPC ............ *A61K 31/44* (2013.01); *A61K 9/0019* (2013.01); *A61K 9/4833* (2013.01); *A61K 31/661* (2013.01); *A61K 47/543* (2017.08)

(58) Field of Classification Search
CPC ...... A61K 31/445; A61K 47/14; A61K 47/28; A61K 9/127
See application file for complete search history.

(56) References Cited

U.S. PATENT DOCUMENTS

| | | | |
|---|---|---|---|
| 5,316,771 | A | 5/1994 | Barenholz |
| 5,817,074 | A | 10/1998 | Racz |
| 8,182,835 | B2 | 5/2012 | Kim et al. |
| 8,410,104 | B2 | 4/2013 | Brummett |
| 8,834,921 | B2 | 9/2014 | Kim et al. |
| 8,906,966 | B2 | 12/2014 | Sherwood et al. |
| 8,957,779 | B2 | 2/2015 | Wu et al. |
| 8,975,268 | B2 | 3/2015 | Berde et al. |
| 8,975,281 | B2 | 3/2015 | Berde et al. |
| 9,192,575 | B2 | 11/2015 | Kim et al. |
| 9,205,052 | B2 | 12/2015 | Kim et al. |
| 9,585,838 | B2 | 5/2017 | Hartounian et al. |
| 10,398,648 | B2 | 9/2019 | Schutt et al. |
| 11,033,495 | B1 | 1/2021 | Hall et al. |
| 11,179,336 | B1 | 11/2021 | Hall et al. |
| 11,278,494 | B1 | 3/2022 | Hall et al. |
| 11,304,904 | B1 | 4/2022 | Hall et al. |
| 11,311,486 | B1 | 4/2022 | Hall et al. |
| 11,357,727 | B1 | 6/2022 | Hall et al. |
| 11,426,348 | B2 | 8/2022 | Hall et al. |
| 11,452,691 | B1 | 9/2022 | Hall et al. |
| 11,759,459 | B2 | 9/2023 | Winston et al. |
| 2002/0039596 | A1 | 4/2002 | Hartounian et al. |
| 2003/0059462 | A1 | 3/2003 | Barenholz |
| 2003/0069318 | A1 | 4/2003 | Dang et al. |
| 2003/0170288 | A1 | 9/2003 | Carr et al. |
| 2006/0078606 | A1* | 4/2006 | Kim ...................... A61K 31/167 424/450 |
| 2007/0249681 | A1 | 10/2007 | Sudo et al. |
| 2009/0105693 | A1 | 4/2009 | Ben-David et al. |
| 2009/0202436 | A1 | 8/2009 | Hobot et al. |
| 2011/0250264 | A1 | 10/2011 | Schutt et al. |
| 2012/0179038 | A1 | 6/2012 | Meurer et al. |
| 2013/0177633 | A1 | 7/2013 | Schutt et al. |
| 2013/0177634 | A1 | 7/2013 | Schutt et al. |
| 2013/0177635 | A1 | 7/2013 | Schutt et al. |
| 2013/0177636 | A1 | 7/2013 | Schutt et al. |
| 2013/0177637 | A1 | 7/2013 | Schutt et al. |
| 2013/0177638 | A1 | 7/2013 | Schutt et al. |
| 2013/0183372 | A1 | 7/2013 | Schutt et al. |
| 2013/0183373 | A1 | 7/2013 | Schutt et al. |
| 2013/0183375 | A1 | 7/2013 | Schutt et al. |
| 2013/0189349 | A1 | 7/2013 | Kim et al. |
| 2013/0195965 | A1 | 8/2013 | Schutt et al. |
| 2013/0306759 | A1 | 11/2013 | Schutt et al. |
| 2013/0344132 | A1 | 12/2013 | Kim et al. |
| 2014/0296293 | A1 | 10/2014 | Andersen et al. |

(Continued)

FOREIGN PATENT DOCUMENTS

| | | |
|---|---|---|
| CN | 109745607 | 5/2019 |
| RU | 2307675 | 10/2007 |

(Continued)

OTHER PUBLICATIONS

Mayfield Clinic, Mayfield Clinic, 2018 (Year: 2018).*
Rongstad, Foot & Ankle International, vol. 17, No. 7, Jul. 1996 (Year: 1996).*
Fiol, Anesth Pain Res, 2020 vol. 4, Issue 2, pp. 1-6 (Year: 2020).*
Li, BMC Musculoskeletal Disorders, Jan. 2021, 22:735, pp. 1-9 (Year: 2021).*
Worrell, AANA Journal, Apr. 1, 1996, 64(2):146-152 (Year: 1996).*
"Adductor Canal Block: What Nerves Are We After? uploaded on Oct. 2, 2020 by Regional Anesthesiology and Acute Pain Medicine". Retrieved from internet: https://www.youtube.com/watch?v=fE4U7JQa2f8) (hereafter "Regional") (Year: 2020).*
[No Author Listed] [online], "Highlights of Prescribing Information—EXPAREL," accessdata.fda.gov, Apr. 2018, retrieved on Jun. 17, 2022, retrieved from URL <www.accessdata.fda.gov/drugsatfda_docs/label/2018/022496s91bl.pdf>, 28 pages.

(Continued)

*Primary Examiner* — Jean P Cornet
(74) *Attorney, Agent, or Firm* — Fish & Richardson P.C.

(57) ABSTRACT

Provided herein are methods of administering to a peroneal and a tibial nerve of a patient, wherein the methods include: (a) selecting an entry point of an injection needle in a leg of a patient; (b) inserting the injection needle into the patient at the entry point; (c) administering to a sciatic nerve of the patient via the injection needle saline and a pharmaceutical composition; wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome.

30 Claims, 36 Drawing Sheets

(56) References Cited

U.S. PATENT DOCUMENTS

| | | | |
|---|---|---|---|
| 2015/0250724 | A1 | 9/2015 | Yamashita et al. |
| 2016/0000705 | A1 | 1/2016 | McDonald et al. |
| 2016/0089335 | A1 | 3/2016 | Ohri et al. |
| 2016/0361260 | A1 | 12/2016 | Schutt et al. |
| 2016/0375140 | A1 | 12/2016 | Ottoboni et al. |
| 2017/0007549 | A1 | 1/2017 | Yum et al. |
| 2018/0092847 | A1 | 4/2018 | Schutt et al. |
| 2019/0231762 | A1 | 8/2019 | Verity |
| 2022/0015738 | A1 | 1/2022 | Harbi et al. |
| 2022/0096116 | A1 | 3/2022 | McFarland et al. |
| 2022/0273564 | A1 | 5/2022 | Slonin et al. |
| 2022/0218610 | A1 | 7/2022 | Sionin |
| 2022/0218613 | A1 | 7/2022 | Slonin et al. |
| 2022/0387318 | A1 | 12/2022 | Winston |
| 2023/0038098 | A1 | 2/2023 | Winston et al. |
| 2023/0042662 | A1 | 2/2023 | Los et al. |
| 2023/0052319 | A1 | 2/2023 | Winston et al. |
| 2023/0080593 | A1 | 3/2023 | Winston et al. |
| 2023/0087140 | A1 | 3/2023 | Winston et al. |
| 2023/0130180 | A1 | 4/2023 | Los et al. |

FOREIGN PATENT DOCUMENTS

| | | |
|---|---|---|
| WO | WO 1997/003652 | 2/1997 |
| WO | WO 1999/013865 | 3/1999 |
| WO | WO 1999/044640 | 9/1999 |
| WO | WO 2016/174661 | 11/2016 |
| WO | WO 2018/226732 | 12/2018 |
| WO | WO 2018/237109 | 12/2018 |
| WO | WO 2021/141956 | 7/2021 |
| WO | WO 2021/141959 | 7/2021 |
| WO | WO 2021/141963 | 7/2021 |

OTHER PUBLICATIONS

[No Author Listed] [online], "Marcaine [package insert]," accessdata.fda.gov, Oct. 2011, retrieved on Jun. 21, 2022, retrieved from URL <https://www.accessdata.fda.gov/drugsatfda_docs/label/2012/018692s0151bl.pdf>, 30 pages.

[No Author Listed] [online], "Naropin [package insert]," accessdata.fda.gov, Nov. 2018, retrieved on Jun. 21, 2022, retrieved from URL <https://www.accessdata.fda.gov/drugsatfda_docs/label/2018/020533s0351bl.pdf>, 30 pages.

Ahiskalioglu et al., "Can high volume pericapsular nerve group (PENG) block act as a lumbar plexus block?" Journal of Clinical Anesthesia, May 2020, 61:109650, 2 pages.

American Society of Anesthesiologists Task Force on Acute Pain Management, "Practice guidelines for acute pain management in the perioperative setting: an updated report by the American Society of Anesthesiologists Task Force on Acute Pain Management," Anesthesiology, Feb. 2012, 116(2):248-273.

American Society of Anesthesiologists, "ASA Physical Status Classification System," asahq.org, Dec. 13, 2020, retrieved from URL <https://www.asahq.org/standards-and-guidelines/asa-physical-status-classification-system>, 4 pages.

Beachler et al. "Liposomal bupivacaine in total hip arthroplasty: Do the results justify the cost?" Journal of Orthopaedics, 2017, 14:161-165.

Bigeleisen et al., "Novel approaches in pain management in cardiac surgery," Curr Opin Anaesthesiol. Feb. 2015, 28(1):89-94.

Biotechnology Innovation Organization "Re: Docket No. FDA-2019-N-2514: Standards for Future Opioid Analgesic Approvals and Incentives for New Therapeutics to Treat Pain and Addiction," Nov. 18, 2019, 11 pages.

Bronson et al. "Unanticipated transient sciatic nerve deficits from intra-wound liposomal bupivacaine injection during total hip arthroplasty," Arthroplasty Today, 2015, 1:21-24.

Chughtai et al., "Liposomal Bupivacaine Is Both Safe and Effective in Controlling Postoperative Pain After Spinal Surgery in Children: A Controlled Cohort Study," Clin Spine Surg., 2020, 33(10):E533-E538.

Cohen et al., "Incidence of adverse events attributable to bupivacaine liposome injectable suspension or plain bupivacaine for postoperative pain in pediatric surgical patients: A retrospective matched cohort analysis," Paediatr Anaesth., 2019, 29(2):169-174, 15 pages.

Day et al., "Extended Release Liposomal Bupivacaine Injection (Exparel) for Early Postoperative Pain Control Following Pharyngoplasty," J Craniofac Surg., Jul. 2018, 29(3):726-730, 4 pages.

De Leeuw et al., "The Psoas Compartment Block for Hip Surgery: The Past, Present, and Future," Anesthesiology Research and Practice, 2011, Article ID 159541, pp. 1-6.

Delgado et al., "Validation of Digital Visual Analog Scale Pain Scoring With a Traditional Paper-based Visual Analog Scale in Adults," J Am Acad Orthop Surg Glob Res Rev., Mar. 2018, 2(3):e088, 6 pages.

Duzlu et al., "Release Pattern of Liposomal Bupivacaine in Artificial Cerebrospinal Fluid," Turk J Anaesth Reanim., 2016, 44:1-6.

Ecoffey, "Refresher course: Local anesthetic pharmacology in children," Regional Anesthesia and Pain Medicine, 2015, 40(5):e23-e25.

FDA.gov [online] "Methodologies for Determining Opioid Sparing in Acute Pain Models," available on or before Dec. 14, 2019, via Internet Archive: Wayback Machine URL <http://web.archive.org/web/20191214114348/https://www.fda.gov/media/121206/download>, 61 pages.

Gan, "Poorly controlled postoperative pain: prevalence, consequences, and prevention," J Pain Res. 2017, 10:2287-2298.

Gerbershagen et al., "Pain intensity on the first day after surgery: a prospective cohort study comparing 179 surgical procedures," Anesthesiology, Apr. 2013, 118(4):934-944.

Ginosar et al., "ED50 and ED95 of Intrathecal Hyperbaric Bupivacaine Coadministered with Opioids for Cesarean Delivery," Anesthesiology, Mar. 2004, 100(3):676-682.

Giron Arango et al., "Reply to Dr Yu et al: Inadvertent quadriceps weakness following the pericapsular nerve group (PENG) block," Reg Anesth Pain Med, May 2019, 44(5):613-614.

Globalnewswire.com [online], "Pacira—EXPAREL Achieves Primary and Key Secondary Endpoints in Phase 4 CHOICE Study in Cesarean Section Patients," Jan. 7, 2020, retrieved on Apr. 11, 2022, retrieved from URL <https://www.globenewswire.com/news-release/2020/01/07/1967140/0/en/EXPAREL-Achieves-Primary-and-Key-Secondary-Endpoints-in-Phase-4-CHOICE-Study-in-Cesarean-Section-Patients.html>, 6 pages.

Gottschalk et al., "Quality of postoperative pain using an intraoperatively placed epidural catheter after major lumbar spinal surgery," Anesthesiology, Jul. 2004, 101(1):175-180.

Hadzic et al., "Liposome Bupivacaine Femoral Nerve Block for Postsurgical Analgesia after Total Knee Arthroplasty," Anesthesiology, Jun. 2016, 124(6):1372-1383.

Hu et al., "Pharmacokinetic profile of liposome bupivacaine injection following a single administration at the surgical site," Clin Drug Investig., 2013, 33(2):109-115.

International Preliminary Report on Patentability in International Appln. No. PCT/US2021/012266, dated Jul. 12, 2022, 14 pages.

International Preliminary Report on Patentability in International Appln. No. PCT/US2021/012269, dated Jul. 21, 2022, 23 pages.

International Preliminary Report on Patentability in International Appln. No. PCT/US2021/012275, dated Jul. 12, 2022, 13 pages.

International Search Report and Written Opinion in International Appln. No. PCT/US2021/012266, dated Apr. 30, 2021, 16 pages.

International Search Report and Written Opinion in International Appln. No. PCT/US2021/012269, dated Mar. 25, 2021, 25 pages.

International Search Report and Written Opinion in International Appln. No. PCT/US2021/012275, dated Mar. 25, 2021, 14 pages.

International Search Report and Written Opinion in International Appln. No. PCT/US2022/011828, dated Apr. 1, 2022, 18 pages.

International Search Report and Written Opinion in International Appln. No. PCT/US2022/020713, dated Jun. 14, 2022, 24 pages.

Joshi et al., "The Safety of Liposome Bupivacaine Following Various Routes of Administration in Animals, " Journal of Pain Research, 2015, 8:781-789.

(56) References Cited

OTHER PUBLICATIONS

Laura Giron-Arango et al., "Pericapsular Nerve Group (PENG) Block for Hip Fracture", Reg Anesth Pain Med, 2018, 43:859-863, 5 pages.

Li et al., "Acute postoperative opioid consumption trajectories and long-term outcomes in pediatric patients after spine surgery," J Pain Res., 2019, 12:1673-1684.

Malik et al., "Emerging roles of liposomal bupivacaine in anesthesia practice," Journal of Anaesthesiology Clinical Pharmacology, Apr. 0Jun. 2017, 33(2):151-156.

Malinovsky et al., "Neurotoxicological Assessment After Intracisternal Injection of Liposomal Bupivacaine in Rabbits," Anesth. Analg., 1997, 85:1331-1336.

Manna et al., "Probing the mechanism of bupivacaine drug release from multivesicular liposomes," J Control Release, Jan. 28, 2019, 294:279-287, 41 pages.

Mannion et al., "In with the New, Out with the Old? Comparison of Two Approaches for Psoas Compartment Block," Anesthesia and Analgesia, 2005, 101:259-264.

Mannion, "Psoas Compartment Block," Continuing Education in Anesthesia, Critical Care & Pain, 2007, 7(5):162-166.

Mazoit et al., "Pharmacokinetics of bupivacaine following caudal anesthesia in infants," Anesthesiology, Mar. 1, 1988, 68(3):387-391.

McGraw-Tatum et al. "A Prospective, Randomized Trial Comparing Liposomal Bupivacaine vs Fascia Iliaca Compartment Block for Postoperative Pain Control in Total Hip Arthroplasty," The Journal of Arthroplasty, 2017, 32:2181-2185.

Nedeljkovic et al., "Liposomal Bupivacaine Transversus Abdominis Plane Block for Pain After Cesarean Delivery: Results From a Multicenter, Randomized, Double-Blind, Controlled Trial," PowerPoint, Presented at Society for Obstetric Anesthesia and Perinatology 51st Annual Meeting, Phoenix, AZ, May 1-5, 2019, 17 pages.

Nedeljkovic et al., "Transversus Abdominis Plane Block With Liposomal Bupivacaine for Pain After Cesarean Delivery in a Multicenter, Randomized, Double-Blind, Controlled Trial," Anesth. Analg., Dec. 2020, 131(6):1830-1839.

Oda, "Pharmacokinetics and systemic toxicity of local anesthetics in children," Journal of anesthesia, Jun. 16, 2016, 30(4):547-550.

Peng et al., "Reply to Dr Nielsen: Pericapsular Nerve Group (PENG) block for hip fracture," Reg Anesth Pain Med, Mar. 2019, 44(3):415-416.

Perets et al. "Intraoperative Infiltration of Liposomal Bupivacaine vs Bupivacaine Hydrochloride for Pain Management in Primary Total Hip Arthroplasty: A Prospective Randomized Trial," The Journal of Arthroplasty, 2018, 33:441-446.

Rabbitts et al., "Presurgical psychosocial predictors of acute postsurgical pain and quality of life in children undergoing major surgery," J Pain., Mar. 2015, 16(3):226-234.

Rabbitts et al., "Trajectories of postsurgical pain in children: risk factors and impact of late pain recovery on long-term health outcomes after major surgery," Pain, Nov. 2015, 156(11):2383-2389.

Raja et al., "The revised International Association for the Study of Pain definition of pain: concepts, challenges, and compromises," PAIN, Sep. 1, 2020, 161(9):1976-1982.

Rice et al., "Pharmacokinetic Profile and Tolerability of Liposomal Bupivacaine Following a Repeated Dose via Local Subcutaneous Infiltration in Healthy Volunteers," Clin Drug Investig., 2017, 37(3):249-257.

Santos et al., "Is Continuous PENG Block the New 3-in-1?" J Anesth Clin Res 2019, Jun. 28, 2019, 10(6):1000898 , 2 pages.

Scott et al., "Acute Toxicity of Ropivacaine Compared with that of Bupivacaine," Anesthesia and Analgesia, Nov. 1, 1989, 69(5):563-569.

Shah et al., "Current Trends in Pediatric Spine Deformity Surgery: Multimodal Pain Management and Rapid Recovery," Global Spine J., 2020, 10(3):346-352.

Short et al., "Anatomic Study of Innervation of the Anterior Hip Capsule: Implication for Image-Guided Intervention," Regional Anesthesia and Pain Medicine, Feb. 2018, 43(2):186-192.

Springer et al., "Systemic Safety of Liposomal Bupivacaine in Simultaneous Bilateral Total Knee Arthroplasty," J Arthroplasty., Jan. 2018, 33(1):97-101.

Surdam et al., "The Use of Exparel (Liposomal Bupivacaine) to Manage Postoperative Pain in Unilateral Total Knee Arthroplasty Patients," Journal of Arthroplasty, 2015, 30:325-329.

Therapy Services Patient Information [online] "Pubic Rami Fracture," retrieved on Jan. 11, 2023, retrieved from URL <https://www.uhd.nhs.uk/uploads/about/docs/our_publications/patient_information_leaflets/orthopaedics/Pubic_rami_fracture.pdf>, 12 pages.

Tirotta et al., "Continuous incisional infusion of local anesthetic in pediatric patients following open heart surgery," Pediatr Anaesth., Jun. 2009, 19(6):571-576.

Tran et al . . . , "Is pericapsular nerve group (PENG) block a true pericapsular block?," Reg Anesth Pain Med, Feb. 2019, 44(2):257.

USFaD, "Pediatric Study Plans: Content of and Process for Submitting Initial Pediatric Study Plans and Amended Initial Pediatric Study Plans Guidance for Industry," US Food and Drug Administration, Jul. 2020, retrieved from URL <https://www.fda.gov/media/86340/download>, 26 pages.

Walker et al., "Complications in Pediatric Regional Anesthesia: An Analysis of More than 100,000 Blocks from the Pediatric Regional Anesthesia Network," Anesthesiology, Oct. 2018, 129(4):721-732.

www.sec.gov [online], "Pacira BioSciences Reports First Quarter 2019 Revenues of $91.3 Million," May 2019, retrieved on Sep. 30, 2022, retrieved from URL <https://www.sec.gov/Archives/edgar/data/1396814/000139681419000012/pcrx-3312019x991.htm>, 12 pages.

Yu et al., "Inadvertent quadriceps weakness following the pericapsular nerve group (PENG) block," Reg Anesth Pain Med, May 2019, 44(5):611-613.

Zel et al., "Neurological and Histological Outcomes After Subarachnoid Injection of a Liposomal Bupivacaine Suspension in Pigs: A Pilot Study," British Journal of Anaesthesia, Mar. 2019, 122(3):379-387.

Tong et al., "Liposomal bupivacaine and clinical outcomes," Best Practice & Research Clinical Anaesthesiology, 2014, 28:15-17.

[No Author Listed] [online], "Full Prescribing Information—Exparel," exparel.com, revised Mar. 2022, retrieved on Apr. 14, 2022, retrieved from URL <https://www.exparel.com/hcp/prescribing-information.pdf?msclkid=60c82e5b2c231a2fdbe94c034f355fb2&utm_source=bing&utm_medium=cpc&utm_campaign=HCP%20-%20Branded&utm_term=exparel%20dosing%20information&utm_content=Dosage>, 36 pages.

Kim et al., "Preparation of multivesicular liposomes," Biochim. Biophys. Acta., Mar. 1983, 728(3):339-348.

Patel et al., "Brachial Plexus Block with Liposomal Bupivacaine for Shoulder Surgery Improves Analgesia and Reduces Opioid Consumption: Results from a Multicenter, Randomized, Double-Blind, Controlled Trial," Pain Med., 2020, 21(2):387-400.

Domb et al., "The effect of liposomal bupivacaine injection during total hip arthroplasty: a controlled cohort study," BMC Musculosketeal Disorders, 2014, 15(310):1-6.

[No Author Listed] [online], "Adductor Canal Block," RAUKvideos, uploaded on Jan. 29, 2021, retrieved on May 25, 2023, retrieved from URL <https://www.youtube.com/watch?v=DZLjNHkbMtl>, 2 pages [Video Submission].

[No Author Listed] [online], "Adductor Canal Block: What Nerves Are We After?," Regional Anesthesiology and Acute Pain Medicine, uploaded on Oct. 2, 2020, retrieved from internet on May 25, 2023, retrieved from URL <https://www.youtube.com/watch?v=fE4U7JQa2f8>, 2 pages [Video Submission].

Acharya et al., "Pericapsular Nerve Group Block: An Excellent Option for Analgesia for Positional Pain in Hip Fractures," Case Reports in Anesthesiology, Mar. 12, 2020, 2020,(1830136):1-3.

Ackmann et al., "Anatomy of the Infrapatellar Branch in Relation to Skin Incisions and as the Basis to Treat Neuropathic Pain by Percutaneous Cryodenervation," Pain Physician Journal, May/Jun. 2014, 17:E229-E348.

Bagaria et al., "The feasibility of direct adductor canal block (DACB) as a part of periarticular injection in total knee arthroplasty," Knee Surgery & Related Research, 2020, 32(48), 7 pages.

(56) References Cited

OTHER PUBLICATIONS

Chin et al., "Mechanisms of action of fascial plane blocks: a narrative review," Regional Anesthesia and Pain Medicine, 2021, 46:618-628.

Greenky et al., "Intraoperative Surgeon Administered Adductor Canal Blockade Is Not Inferior to Anesthesiologist Administered Adductor Canal Blockade: A Prospective Randomized Trial," The Journal of Arthroplasty, 2020, 35:1228-1232.

Matthews et al., "Surgeon-placed peripheral nerve block and continuous non-opioid analgesia in total knee arthroplasty is accessible intraoperatively: A cadaveric study," Journal of ISAKOS, Mar. 2023, 6 pages.

Matthews, "Continuous Adductor Canal & Periarticular Nerve Block for Total Knee Arthroplasty, Matthews' Placement Guide," Surgical Solutions, 2021, 6 pages.

Mont et al., "Can Joint Arthroplasty Surgeons Safely Administer Anesthesia?," The Journal of Arthroplasty, 2020, 35:1169.

Pepper et al., "Intraoperative Adductor Canal Block for Augmentation of Periarticular Injection in Total Knee Arthroplasty: A Cadaveric Study," The Journal of Arthroplasty, 2016, 31:2072-2076.

Peterson et al., "Surgeon-Performed High-Dose Bupivacaine Periarticular Injection with Intra-Articular Saphenous Nerve Block is Not Inferior to Adductor Canal Block in Total Knee Arthroplasty," The Journal of Arthroplasty, May 2020, 35:1233-1238.

Runge et al., "The Spread of Ultrasound-Guided Injectate From the Adductor Canal to the Genicular Branch of the Posterior Obturator Nerve and the Popliteal," Regional Anesthesia and Acute Pain, Dec. 2017, 42(6):725-730.

Sveom et al., "Ultrasound-Guided Adductor Canal Block Versus Intraoperative Transarticular Saphenous Nerve Block: A Retrospective Analysis," The Journal of Arthroplasty, 2022, 37:S134-S138.

Tak et al., "Continuous adductor canal block is superior to adductor canal block alone or adductor canal block combined with IPACK block (interspace between the popliteal artery and the posterior capsule of knee) in postoperative analgesia and ambulation following continued from U): total knee arthroplasty: randomized control trial," Musculoskeletal Surg., Jun. 2022, 106:155-162.

Teachmeanatomy.info [online], "Anatomical Planes," Sep. 30, 2022, retrieved on Jun. 13, 2023, retrieved from URL <https://teachmeanatomy.info/the-basics/anatomical-terminology/planes/>, 2 pages.

Tran et al., "Evaluation of the proximal adductor canal block injectate spread: a cadaveric study," Reg. Anesth. Pain. Med., 2020, 45:124-130.

Yee et al., "Quadriceps Weakness After Single-Short Adductor Canal Block," The Journal of Bone and Joint Surgery, 2021, 103(1):30-36.

U.S. Appl. No. 17/684,805, filed Mar. 20, 2022, Slonin et al.
U.S. Appl. No. 17/719,716, filed Apr. 13, 2022, Hall et al.
U.S. Appl. No. 17/720,166, filed Apr. 13, 2022, Hall et al.
U.S. Appl. No. 17/840,104, filed Jun. 14, 2022, Hall et al.
U.S. Appl. No. 18/046,416, filed Oct. 13, 2022, Garcia et al.
U.S. Appl. No. 18/325,924, filed May 30, 2023, Hall et al.
U.S. Appl. No. 18/325,927, filed May 30, 2023, Hall et al.

Epstein et al., "Plasma Bupivacaine Concentrations Following Iioinguinal-Iliohypogastric Nerve Blockade in Children," Anesthesiology, Nov. 1, 1988, 69(5):773-776.

International Preliminary Report on Patentability in International Application No. PCT/US2022/020713, dated Sep. 28, 2023, 18 pages.

Kanazi et al., "The Analgesic Efficacy of Subarachnoid Morphine in Comparison with Ultrasound-Guided Transversus Abdominis Plane Block After Cesarean Delivery A Randomized Controlled Trial," Anesthesia & Analgesia, Aug. 201, 111(2):475-481.

Medilogbiohealth.com [online], "Angles of Administration of Injection—ID, IM, SC, IV," Mar. 10, 2021, retrieved on Aug. 22, 2023, retrieved from URL <https://www.medilogbiohealth.com/2021/03/injection.html>, 8 pages.

Stow et al., "Plasma bupivacaine concentrations during caudal analgesia and ilioniguinal-iliohypogastric nerve block in children," Anaesthesia, Aug. 1998, 43(8):650-653.

Vij et al., Liposomal Bupivacaine Decreases Post-Operative Opioid Use after Anterior Cruciate Ligament Reconstruction: A Review of Level I Evidence, Orthopedic Reviews, Aug. 5, 2022, 14(3):37159, 8 pages.

\* cited by examiner

Table 1 - Schedule of Assessments (Screening through Day 14)

| | Screening Visit¹ | Day of Surgery (Prior to Surgery) | OR | PACU | 6 ±2 | 12 ±2 | 18 ±2 | 24 ±2 | 30 ±2 | 36 ±2 | 42 ±2 | 48 ±2 | 54 ±2 | 60 ±2 | 66 ±2 | 72 ±2 | 78 ±3 | 84 ±3 | 90 ±3 | 96 ±3 | 120-168 ±3² | Health Care Facility Discharge³ | POD14 Call ±3 days |
|---|---|---|---|---|---|---|---|---|---|---|---|---|---|---|---|---|---|---|---|---|---|---|---|
| Obtain ICF* | X | | | | | | | | | | | | | | | | | | | | | | |
| Assess/confirm eligibility* | X | X⁴ | | | | | | | | | | | | | | | | | | | | | |
| Record medical/surgical history*⁵ | X | | | | | | | | | | | | | | | | | | | | | | |
| Collect height/weight for BMI calculation* | X | | | | | | | | | | | | | | | | | | | | | | |
| Demographics and baseline characteristics* | X | | | | | | | | | | | | | | | | | | | | | | |
| Record prior and concomitant medications⁵ | X | X⁴ | ◄-------------------------------------------------------------------------------------------------------------► |
| Urine pregnancy test for WOCBP | X | X⁴ | | | | | | | | | | | | | | | | | | | | | |
| Urine drug screen | | X⁴ | | | | | | | | | | | | | | | | | | | | | |
| Perform 12-lead EKG⁶ | X | | | | | | | X | | | | X | | | | X | | | X | X | | | |
| Review Pain Rating Guide | | X⁴ | | | | | | | | | | | | | | | | | | | | | |
| Record worst and average pain (NRS) in the last 30 days | | X⁴ | | | | | | | | | | | | | | | | | | | | | |
| Randomize subject; prepare study drug | | X | | | | | | | | | | | | | | | | | | | | | |
| Record pre-op and post-op scheduled medications⁷ | | X | ◄-----► | | | | | | | | | | | | | | | | | | | |
| Capture ultrasound video for nerve block and send to Sponsor | | X | | | | | | | | | | | | | | | | | | | | | |

FIG. 1

Table 1 - Schedule of Assessments (Screening through Day 14)

| | Screening Visit[1] | Day of Surgery (Prior to Surgery) | OR | PACU | 6 ±2 | 12 ±2 | 18 ±2 | 24 ±2 | 30 ±2 | 36 ±2 | 42 ±2 | 48 ±2 | 54 ±2 | 60 ±2 | 66 ±2 | 72 ±2 | 78 ±3 | 84 ±3 | 90 ±3 | 96 ±3 | 120-168 ±3[2] | Health Care Facility Discharge[3] | POD14 Call ±3 days |
|---|---|---|---|---|---|---|---|---|---|---|---|---|---|---|---|---|---|---|---|---|---|---|---|
| Administer Mayo field block | | | X | | | | | | | | | | | | | | | | | | | | |
| Record block start/end times[8] | | | X | X | | | | | | | | | | | | | | | | | | | |
| Record surgery start and end times | | | X | | | | | | | | | | | | | | | | | | | | |
| Record intra-op medication administered | | | X | | | | | | | | | | | | | | | | | | | | |
| Record PACU time in and out | | | | X | | | | | | | | | | | | | | | | | | | |
| Record scheduled NRS scores[9,10] | | | | X | X | X | X | X | X | X | X | X | X | X | X | X | X | X | X | X | | | |
| Measure and record vital signs[11] | | X[4] | | X | X | X | X | X | X | X | X | X | X | X | X | X | X | X | X | X | X | X | |
| Record scheduled worst and average NRS scores (24-h recall)[9,10] | | | | | | | | X | | | | X | | | | X | | | | X | | | |
| Record unscheduled NRS immediately prior to breakthrough pain medication[12] | | | | ◄----------------------------------------------------------------------------------► | | | | | | | | | | | | | | | | | | |
| Record breakthrough pain medication[12] | | | | ◄----------------------------------------------------------------------------------► | | | | | | | | | | | | | | | | | | |
| Record day and time of HCF admission and discharge | | X | | | | | | | | | | | | | | | | | | | | X | |
| Record AEs/SAEs[13] | ◄--------------------------------------------------------------------------------------------------------------------------------------------------------------------------------------------------► |

FIG. 1 (Cont.)

Table 1 - Schedule of Assessments (Screening through Day 14)

| | Screening Visit[1] | Day of Surgery (Prior to Surgery) | OR | PACU | 6 ±2 | 12 ±2 | 18 ±2 | 24 ±2 | 30 ±2 | 36 ±2 | 42 ±2 | 48 ±2 | 54 ±2 | 60 ±2 | 66 ±2 | 72 ±2 | 78 ±2 | 84 ±3 | 90 ±3 | 96 ±3 | 120-168 ±3[2] | Health Care Facility Discharge[3] | POD14 Call ±3 days |
|---|---|---|---|---|---|---|---|---|---|---|---|---|---|---|---|---|---|---|---|---|---|---|---|
| | | | | | | | | | | | | | Time From End of Surgery (h) | | | | | | | | | | |
| Perform unscheduled neurological assessment[14] | | ←------|-----|-----|-----|-----|-----|-----|-----|-----|-----|-----|-----|-----|-----|-----|-----|-----|-----|-----|-----|-----|→ |
| Subject satisfaction questionnaire (IPO) | | | | | | | | | | | | | | | | | | | | X | | | |

Abbreviations: AE = adverse event; AESI = adverse event of special interest; BMI = body mass index; EKG = electrocardiogram; h = hour(s); HCF = health care facility; ICF = informed consent form; Intra-op = intra-operative; IPO = International Pain Outcome; IV = intravenously; min = minute(s); NRS = numeric rating scale; OR = Operating Room; PACU = Post-anesthesia Care Unit; PK = pharmacokinetics; PO = by mouth/orally administered; POD = Post-operative Day; Post-op = post-operative; Pre-op = pre-operative; PRN = as needed; SAE = serious adverse event; WOCBP = women of child-bearing potential.

\* No more than 45 days before scheduled surgery day

1 Subjects could be screened on the same day as HCF admission/surgery (with ample time for the informed consent process) or up to 45 days prior to surgery but eligibility was to be re-confirmed on day of the surgery prior to randomization. Screening procedures that were standard of care at the institution could be completed prior to written informed consent. Any screening procedures that were not standard of care were to be completed after written informed consent was obtained.

2 For Part A subjects only: A 12-lead EKG was performed, and vital signs were measured and recorded at additional time points 120 h (±3 h), 144 h (±3 h), and at 168 h (±3 h).

3 Subjects in Part A and Part B were discharged after 168 h and 96 h assessments, respectively.

4 Eligibility, prior medications, urine pregnancy test and urine drug screen were to be assessed prior to randomization; review of Pain Rating Guide and worst and average pain scores over the previous 30 days were to be assessed prior to study drug administration.

5 Relevant medical/surgical history within the last 5 years (including all ongoing history, regardless of start date) were to be recorded, with the exception of history that was relevant to the surgery, in which case all years were to be recorded. Prior medications taken within 30 days of randomization (including all ongoing medications, regardless of start date) were recorded.

6 A baseline 12-lead EKG was performed at the Screening Visit. A 12-lead EKG was performed if a subject experienced an AESI or an SAE (see footnote 15).

7 All pre-operative and post-operative scheduled analgesic medication (celecoxib and acetaminophen) were recorded.

8 Block to be administered 90 min (±30 min) prior to surgery.

9 The NRS pain intensity assessment was not to be completed after any physical activity, including the motor block assessment. If that was not possible, to assess pain intensity at rest, the subject was to rest quietly in a supine or seated position that did not exacerbate subject's postsurgical pain for 5 to 10 mins before assessing the pain score using the NRS. If a subject was asleep, the subject was not to be awakened to assess pain. If the subject awakened within the assessment window, a pain score was collected then.

10 Pain scores (24 h recall) once daily (i.e., worst/average pain) were collected at 24 (±2 h), 48 (±2 h), 72 (±2 h), and 96 (±3 h) post-surgery. Pain scores (current pain) were collected by the study staff beginning at PACU admission (±5 min), q15 min in PACU (±5 min), at PACU discharge (±5 min) then q6h (±2 h) from end of surgery to 72 h post-surgery and q6h (±3 h) from 78-96 h post-surgery.

11 Vital signs (temperature, resting heart rate, respiratory rate, oxygen saturation and blood pressure) were measured after the subject had rested in a supine position for at least 5 mins. Vital signs were measured before study drug administration, upon arrival in the PACU (±5 min), at PACU discharge (±5 min), then q6h (±2 h) from end of surgery

FIG. 1 (Cont.)

Table 1 - Schedule of Assessments (Screening through Day 14)

| | Screening Visit[1] | Day of Surgery (Prior to Surgery) | OR | PACU | \multicolumn{17}{c|}{Time From End of Surgery (h)} | Health Care Facility Discharge[3] | POD14 Call ±3 days |
|---|---|---|---|---|---|---|---|---|---|---|---|---|---|---|---|---|---|---|---|---|---|---|
| | | | | | 6 ±2 | 12 ±2 | 18 ±2 | 24 ±2 | 30 ±2 | 36 ±2 | 42 ±2 | 48 ±2 | 54 ±2 | 60 ±2 | 66 ±2 | 72 ±2 | 78 ±3 | 84 ±3 | 90 ±3 | 96 ±3 | 120-168 ±3[2] | | | to 72 h post-surgery and q6h (±3 h) from 78-96 h post-surgery, and at hospital discharge; additionally, for Part A subjects: 120 h (±3 h), 144 h (±3 h), and 168 h (±3 h). Vital signs were measured and recorded if a subject experienced an AESI or an SAE (see footnote 15).

12 Oxycodone was administered (PRN) for breakthrough pain through 96 h post-surgery; opioids were not to be given on a pre-determined schedule. Immediate release oral (PO) oxycodone was administered in a stepwise approach as follows:
- Initial dose of 5 mg oxycodone could be offered.
- If the initial opioid dose was insufficient for pain relief, an additional 5 mg oxycodone could be offered up to a maximum of 10 mg (total dose).
- If a subject was unable to tolerate PO medication (or the PO oxycodone pain relief is insufficient), IV morphine (initiated at 2 mg) or hydromorphone (initiated at 0.2 mg) could be administered.

13 All AEs with an onset after the subject was randomized and SAEs with an onset after the subject signed the ICF were to documented.

14 An unscheduled neurological assessment was conducted once daily if a subject experienced an AESI or an SAE, until resolution of symptoms (see footnote 15).

15 In case an AESI or SAE occurred during the study, if the Investigator or Medical Monitor considered that the event may be related to study treatment or suggested the possible occurrence of local anesthetic systemic toxicity (with or without the need for treatment [e.g., intralipids]), an unscheduled PK blood sample, 12-lead EKG, and vital signs were collected. Neurological assessments were conducted according to the study site's standard of care at least once daily until resolution of symptoms.

FIG. 1 (Cont.)

Table 2 - Pharmacokinetic and Pharmacodynamic Assessments (Part A Subjects Only)

| Time Window | Post-study Drug Administration[1] ||||||||||||||||||
|---|---|---|---|---|---|---|---|---|---|---|---|---|---|---|---|---|---|---|
| | Day of Study Drug Administration to POD4 |||||||||||||||| POD5 | POD6 | POD7 |
| | Up to 15m before blocks | 15m | 30m | 45m | 1h | 2h | 8h | 12h | 24h | 30h | 48h | 60h | 72h | 84h | 96h | 120h | 144h | 168h |
| | | ±5m | ±5m | ±5m | ±15m | ±30m | ±30m | ±30m | ±1h | ±1h | ±1h | ±2h | ±2h | ±2h | ±3h | ±3h | ±3h | ±3h |
| Collect PK blood sample; record date and time of blood sample[2] | X | | X | X | X | X | X | X | X | X | X | X | X | X | X | X | X | X |
| Assess and record sensory and motor function[3,4] | X | X | X | X | X | X | X | X | X | X | X | X | X | X | X | X | X | X |

Abbreviations: AESI = adverse event of special interest; h = hour(s); m = minute(s); PK = pharmacokinetic; POD = Post-operative Day; SAE = serious adverse event.
1. All time points were from end of block administration.
2. An unscheduled PK sample was to be collected if a subject experienced an AESI or an SAE (see footnote 15 in Table 2).
3. Once the offset of light touch sensation was recorded and documented in both locations, no further scheduled sensory assessments were required. Once the offset of motor block was recorded and documented, no further scheduled motor assessments were required. Pharmacodynamic assessments were to be performed by blinded, trained, licensed medical staff (e.g., Physician, Registered Nurse, Physician Assistant) and documented on the Investigator's study delegation log. A limited number of study staff were to perform the sensory/motor assessments.
4. When subject was in surgery, no sensory or motor function assessments were to be conducted.

FIG. 2

Table 3 - Summary of Demographics (Efficacy Analysis Set)

| | Part A | | | Part A + B | | |
|---|---|---|---|---|---|---|
| | BUP50 N = 22 | EXP133 N = 22 | EXP266[1] N = 22 | EXP133 N = 81 | BUP50 N = 82 | Total N = 185 |
| Age (years); n | 22 | 22 | 22 | 81 | 82 | 185 |
| Mean (SD) | 44.14 (11.639) | 50.95 (12.089) | 48.36 (10.896) | 50.15 (12.823) | 47.24 (11.950) | 48.65 (12.239) |
| Median (Min, max) | 46.00 (23.0, 65.0) | 53.50 (21.0, 67.0) | 50.50 (23.0, 63.0) | 52.00 (18.0, 75.0) | 47.50 (21.0, 76.0) | 50.00 (18.0, 76.0) |
| Age category, n (%) | | | | | | |
| <45 years | 10 (45.5) | 6 (27.3) | 6 (27.3) | 28 (34.6) | 30 (36.6) | 64 (34.6) |
| 45 to <65 years | 11 (50.0) | 15 (68.2) | 16 (72.7) | 45 (55.6) | 47 (57.3) | 108 (58.4) |
| ≥65 years | 1 (4.5) | 1 (4.5) | 0 | 8 (9.9) | 5 (6.1) | 13 (7.0) |
| Sex, n (%) | | | | | | |
| Female | 17 (77.3) | 20 (90.9) | 21 (95.5) | 74 (91.4) | 68 (82.9) | 163 (88.1) |
| Male | 5 (22.7) | 2 (9.1) | 1 (4.5) | 7 (8.6) | 14 (17.1) | 22 (11.9) |
| Ethnicity, n (%) | | | | | | |
| Not Hispanic or Latino | 9 (40.9) | 12 (54.5) | 12 (54.5) | 55 (67.9) | 50 (61.0) | 117 (63.2) |
| Hispanic or Latino | 13 (59.1) | 10 (45.5) | 10 (45.5) | 26 (32.1) | 32 (39.0) | 68 (36.8) |
| Race, n (%) | | | | | | |
| White | 18 (81.8) | 14 (63.6) | 16 (72.7) | 47 (58.0) | 49 (59.8) | 112 (60.5) |
| Black/African American | 4 (18.2) | 7 (31.8) | 4 (18.2) | 25 (30.9) | 28 (34.1) | 57 (30.8) |
| Asain | 0 | 0 | 0 | 4 (4.9) | 1 (1.2) | 5 (2.7) |
| Other/Multiple/Not Reported/Unknown | 0 | 1 (4.5) | 2 (9.1) | 3 (3.7) | 0 | 5 (2.7) |
| American Indian/Alaska Native | 0 | 0 | 0 | 2 (2.5) | 2 (2.4) | 4 (2.2) |
| Native Hawaiian/Other Pacific Islander | 0 | 0 | 0 | 0 | 2 (2.4) | 2 (1.1) |

Abbreviations: Max = maximum; Min = minimum; SD = standard deviation.
1 The EXP266 arm only had subjects in Part A. EXP266 subjects were included in the A + B total.

FIG. 3

Table 4 - Summary of Baseline Characteristics (Efficacy Analysis Set)

| | Part A | | | Part A + B | | |
|---|---|---|---|---|---|---|
| | BUP50 N = 22 | EXP133 N = 22 | EXP266[1] N = 22 | EXP133 N = 81 | BUP50 N = 82 | Total N = 185 |
| ASA Classification, n(%) | | | | | | |
| 1 | 11 (50.0) | 9 (40.9) | 14 (63.6) | 39 (48.1) | 54 (65.9) | 107 (57.8) |
| 2 | 11 (50.0) | 13 (59.1) | 8 (36.4) | 42 (51.9) | 28 (34.1) | 78 (42.2) |
| BMI (kg/m$^2$); n | 22 | 22 | 22 | 81 | 82 | 185 |
| Mean (SD) | 29.93 (4.552) | 29.44 (5.074) | 26.42 (4.025) | 28.74 (5.016) | 27.86 (4.818) | 28.07 (4.853) |
| Median (Min, max) | 30.45 (19.5, 37.1) | 27.75 (21.5, 39.9) | 26.40 (18.4, 33.0) | 28.10 (19.4, 39.9) | 27.70 (19.4, 37.9) | 27.50 (18.4, 39.9) |
| BMI category, n (%) | | | | | | |
| <25 kg/m$^2$ | 2 (9.1) | 4 (18.2) | 8 (36.4) | 21 (25.9) | 24 (29.3) | 53 (28.6) |
| 25 to <30 kg/m$^2$ | 9 (40.9) | 8 (36.4) | 10 (45.5) | 27 (33.3) | 32 (39.0) | 69 (37.3) |
| ≥30 kg/m$^2$ | 11 (50.0) | 10 (45.5) | 4 (18.2) | 33 (40.7) | 26 (31.7) | 63 (34.1) |
| Worst pain intensity[2] (NRS); n | 21 | 22 | 22 | 81 | 81 | 184 |
| Mean (SD) | 5.6 (2.29) | 5.5 (2.74) | 5.4 (3.00) | 5.2 (2.71) | 5.7 (2.59) | 5.5 (2.69) |
| Median (Min, max) | 5.0 (0, 10) | 6.0 (0, 10) | 5.5 (0, 10) | 6.0 (0, 10) | 6.0 (0, 10) | 6.0 (0, 10) |
| Average pain intensity[2] (NRS); n | 21 | 22 | 22 | 81 | 81 | 184 |
| Mean (SD) | 3.8 (2.19) | 3.8 (2.07) | 3.9 (2.23) | 3.4 (2.10) | 3.8 (2.23) | 3.7 (2.22) |
| Median (Min, max) | 4.0 (0, 8) | 4.0 (0, 7) | 4.5 (0, 7) | 4.0 (0, 8) | 4.0 (0, 10) | 4.0 (0, 10) |

Abbreviations: ASA = American Society of Anesthesiologists; BMI = body mass index; Max = maximum; Min = minimum; NRS = Numeric Rating Scale; SD = standard deviation.
1 The EXP266 arm only had subjects in Part A. EXP266 subjects were included in the A + B total.
2 In the last 30 days.

FIG. 4

Table 5 - AUC of NRS Pain Intensity 0-96h Post-surgery – Part A, Part B (Efficacy Analysis Set)

| Part A | EXP266 (N = 22) | EXP133 (N = 22) | BUP50 (N = 22) |
|---|---|---|---|
| AUC of NRS Pain Intensity Score[1]; n | 22 | 22 | 22 |
| Mean (SD) | 342.3 (265.35) | 211.8 (171.24) | 412.7 (166.80) |
| Median (Min, max) | 264.7 (30, 820) | 200.9 (0, 687) | 447.0 (0, 734) |
| LSM (SE)[2] | 343.3 (42.76) | 217.3 (43.29) | 406.3 (43.50) |
| 95% CI | 259.4, 427.1 | 132.4, 302.1 | 321.0, 491.5 |
| LSM diff from bupivacaine (SE)[2] | -63.0 (61.16) | -189.0 (62.27) | |
| 95% CI | -182.9, 56.9 | -311.0, -67.0 | |
| p-value[3] | 0.1515 | 0.0012 | |

| Part B | | EXP133 (N = 59) | BUP50 (N = 60) |
|---|---|---|---|
| AUC of NRS Pain Intensity Score[1]; n | | 59 | 60 |
| Mean (SD) | | 197.4 (184.49) | 364.5 (195.70) |
| Median (Min, max) | | 143.7 (0, 686) | 371.2 (0, 853) |
| LSM (SE)[2] | | 200.9 (23.34) | 361.1 (23.14) |
| 95% CI | | 155.2, 246.7 | 315.7, 406.4 |
| LSM diff from bupivacaine (SE)[2] | | -160.2 (32.90) | |
| 95% CI | | -224.6, -95.7 | |
| p-value[3] | | <0.00001 | |

Abbreviations: ANCOVA = analysis of covariance; AUC = area under the curve; CI = confidence interval; Diff = difference; h = hour(s); $H_a$ = alternative hypothesis; HCl = hydrochloride; LSM = least squares mean; Max = maximum; Min = minimum; NRS = Numeric Rating Scale; SE = standard error; SD = standard deviation. NRS goes from 0 (no pain) to 10 (worst possible pain). Duplicate score was removed and worst score was retained if it was collected with the same date/time of another score.
1 Area under the pain time curve was calculated using the trapezoidal method for the imputed data.
2 From an ANCOVA with mean effect of treatment and covariate of age.
3 1-sided test for $H_a$: mean AUC for EXPAREL < mean AUC for bupivacaine HCl.

FIG. 5

Table 6 - AUC of NRS Pain Intensity by Time Interval – Part A + B (Efficacy Analysis Set)

| AUC of NRS Pain Intensity Score[1] | EXP133 (N = 81) | BUP50 (N = 82) | 95% CI | p-value[2] | % Reduct in LSM[3] |
|---|---|---|---|---|---|
| At 0-24 h post-surgery; n | 81 | 82 | | | |
| Mean (SD) | 48.3 (43.54) | 46.8 (44.40) | | | |
| Median (Min, max) | 42.8 (0, 158) | 38.3 (0, 189) | | | |
| LSM (SE)[5] | 49.1 (4.80) | 46.0 (4.78) | | | |
| LSM diff from bupivacaine (SE)[4] | 3.2 (6.80) | | -10.2, 16.5 | 0.6785 | -6.74 |
| At 0-48 h post-surgery; n | 81 | 82 | | | |
| Mean (SD) | 122.2 (98.67) | 183.6 (90.32) | | | |
| Median (Min, max) | 101.3 (0, 333) | 182.8 (0, 429) | | | |
| LSM (SE)[5] | 124.8 (10.18) | 181.0 (10.12) | | | |
| LSM diff from bupivacaine (SE)[4] | -56.1 (14.40) | | -84.4, -27.9 | 0.00005 | 31.05 |
| At 0-72 h post-surgery; n | 81 | 82 | | | |
| Mean (SD) | 163.9 (140.52) | 293.8 (139.59) | | | |
| Median (Min, max) | 143.7 (0, 524) | 293.0 (0, 639) | | | |
| LSM (SE)[5] | 168.3 (14.95) | 289.4 (14.86) | | | |
| LSM diff from bupivacaine (SE)[4] | -121.0 (21.15) | | -162.5, -79.6 | <0.00001 | 41.85 |
| At 0-96 h post-surgery; n | 81 | 82 | | | |
| Mean (SD) | 201.3 (180.05) | 377.4 (188.60) | | | |
| Median (Min, max) | 180.7 (0, 687) | 386.4 (0, 853) | | | |
| LSM (SE)[5] | 207.4 (19.61) | 371.4 (19.49) | | | |
| LSM diff from bupivacaine (SE)[4] | -164.0 (27.74) | | -218.3, -109.6 | <0.00001 | 44.16 |

FIG. 6

Table 6 - AUC of NRS Pain Intensity by Time Interval – Part A + B (Efficacy Analysis Set)

| AUC of NRS Pain Intensity Score[1] | EXP133 (N = 81) | BUP50 (N = 82) | 95% CI | p-value[2] | % Reduct in LSM[3] |
|---|---|---|---|---|---|
| At 24-48 h post-surgery; n | 81 | 82 | | | |
| Mean (SD) | 73.9 (62.86) | 136.7 (56.65) | | | |
| Median (Min, max) | 69.7 (0, 216) | 138.2 (0, 240) | | | |
| LSM (SE)[5] | 75.7 (6.41) | 135.0 (6.37) | | | |
| LSM diff from bupivacaine (SE)[4] | -59.3 (9.07) | | -77.1, -41.5 | <0.00001 | 43.93 |
| At 24-72 h post-surgery; n | 81 | 82 | | | |
| Mean (SD) | 115.6 (108.65) | 246.9 (108.59) | | | |
| Median (Min, max) | 99.9 (0, 407) | 253.6 (0, 457) | | | |
| LSM (SE)[5] | 119.2 (11.56) | 234.4 (11.49) | | | |
| LSM diff from bupivacaine (SE)[4] | -124.2 (16.36) | | -156.3, -92.1 | <0.00001 | 51.03 |
| At 24-96 h post-surgery; n | 81 | 82 | | | |
| Mean (SD) | 153.0 (151.14) | 330.6 (158.52) | | | |
| Median (Min, max) | 132.4 (0, 637) | 333.5 (0, 664) | | | |
| LSM (SE)[5] | 158.3 (16.44) | 325.4 (16.34) | | | |
| LSM diff from bupivacaine (SE)[4] | -167.1 (23.26) | | -212.7, -121.5 | <0.00001 | 51.35 |
| At 48-72 h post-surgery; n | 81 | 82 | | | |
| Mean (SD) | 41.7 (51.19) | 110.2 (58.92) | | | |
| Median (Min, max) | 19.2 (0, 193) | 111.8 (0, 217) | | | |
| LSM (SE)[5] | 43.5 (5.89) | 108.4 (5.85) | | | |
| LSM diff from bupivacaine (SE)[4] | -64.9 (8.33) | | -81.2, -48.6 | <0.00001 | 59.87 |

FIG. 6 (Cont.)

Table 6 - AUC of NRS Pain Intensity by Time Interval – Part A + B (Efficacy Analysis Set)

| AUC of NRS Pain Intensity Score[1] | EXP133 (N = 81) | BUP50 (N = 82) | 95% CI | p-value[2] | % Reduct in LSM[3] |
|---|---|---|---|---|---|
| At 48-96 h post-surgery; n | 81 | 82 | | | |
| Mean (SD) | 79.1 (97.59) | 193.9 (112.62) | | | |
| Median (Min, max) | 28.9 (0, 426) | 195.8 (0, 435) | | | |
| LSM (SE)[5] | 82.6 (11.22) | 190.4 (11.15) | | | |
| LSM diff from bupivacaine (SE)[4] | -107.8 (15.87) | | -138.9, -76.7 | <0.00001 | 56.62 |
| At 72-96 h post-surgery; n | 81 | 82 | | | |
| Mean (SD) | 37.4 (49.60) | 83.7 (58.37) | | | |
| Median (Min, max) | 15.1 (0, 233) | 80.7 (0, 221) | | | |
| LSM (SE)[5] | 39.1 (5.79) | 82.0 (5.75) | | | |
| LSM diff from bupivacaine (SE)[4] | -42.9 (8.19) | | -59.0, -26.9 | <0.00001 | 52.32 |

Abbreviations: ANCOVA = analysis of covariance; AUC = area under the curve; CI = confidence interval; Diff = difference; $H_a$ = alternative hypothesis; HCl= hydrochloride; LSM = least squares mean; Max = maximum; Min = minimum; NC = not computed; NRS = Numeric Rating Scale; Reduct = reduction; SE = standard error; SD = standard deviation.
NRS goes from 0 (no pain) to 10 (worst possible pain). Duplicate score was removed and the worst score was retained if it was collected with the same date/time of another score.
1 Area under the pain-time curve was calculated using the trapezoidal method for the imputed data.
2 1-sided p-value for LSM difference. One-sided test for $H_a$ = mean AUC for EXPAREL < mean AUC for bupivacaine HCl.
3 Percent reduction was calculated as (LSM for bupivacaine - LSM for EXPAREL)/LSM for bupivacaine × 100%.
4 From an ANCOVA with mean effect of treatment, categorical covariate of pooled investigator site, and continuous covariate of age.

FIG. 6 (Cont.)

Table 7 - Summary of Total Opioid Consumption by Time Interval (Efficacy Analysis Set)

| Total Opioid Consumption (OMED) | Part A | Part A + B | |
|---|---|---|---|
| | EXP266 (N = 22) | EXP133 (N = 81) | BUP50 (N = 82) |
| At 0-24 h post-surgery; n | 22 | 81 | 82 |
| Geometric mean | 11.29 | 4.44 | 4.52 |
| % CV | 83.495 | 122.216 | 117.479 |
| Median (Min, max) | 7.50 (0.0, 49.5) | 7.50 (0.0, 60.0) | 7.50 (0.0, 51.0) |
| At 0-48 h post-surgery; n | 22 | 81 | 82 |
| Geometric mean | 24.60 | 10.06 | 23.90 |
| % CV | 73.311 | 112.913 | 75.488 |
| Median (Min, max) | 26.25 (0.0, 94.5) | 15.00 (0.0, 85.5) | 33.75 (0.0, 121.5) |
| At 0-72 h post-surgery; n | 22 | 81 | 82 |
| Geometric mean | 28.49 | 12.97 | 34.95 |
| % CV | 89.341 | 121.049 | 78.232 |
| Median (Min, max) | 30.00 (0.0, 147.0) | 15.00 (0.0, 123.0) | 45.00 (0.0, 165.0) |
| At 0-96 h post-surgery; n | 22 | 81 | 82 |
| Geometric mean | 32.68 | 15.41 | 41.62 |
| % CV | 96.768 | 126.781 | 83.925 |
| Median (Min, max) | 30.00 (0.0, 190.5) | 15.00 (0.0, 150.0) | 56.25 (0.0, 246.0) |
| At 24-48 h post-surgery; n | 22 | 81 | 82 |
| Geometric mean | 7.67 | 4.21 | 16.60 |
| % CV | 102.239 | 136.150 | 75.429 |
| Median (Min, max) | 15.00 (0.0, 64.5) | 7.50 (0.0, 60.0) | 22.50 (0.0, 78.0) |
| At 24-72 h post-surgery; n | 22 | 81 | 82 |
| Geometric mean | 11.69 | 6.79 | 27.84 |
| % CV | 120.947 | 148.003 | 79.399 |
| Median (Min, max) | 17.25 (0.0, 117.0) | 7.50 (0.0, 90.0) | 37.50 (0.0, 138.0) |
| At 24-96 h post-surgery; n | 22 | 81 | 82 |
| Geometric mean | 15.99 | 9.00 | 34.65 |
| % CV | 121.894 | 155.556 | 85.902 |
| Median (Min, max) | 22.50 (0.0, 160.5) | 7.50 (0.0, 135.0) | 45.00 (0.0, 231.0) |
| At 48-72 h post-surgery; n | 22 | 81 | 82 |
| Geometric mean | 3.04 | 1.93 | 8.66 |
| % CV | 165.850 | 202.747 | 101.064 |
| Median (Min, max) | 0.00 (0.0, 52.5) | 0.00 (0.0, 37.5) | 15.00 (0.0, 72.0) |

FIG. 7

Table 7 - Summary of Total Opioid Consumption by Time Interval (Efficacy Analysis Set)

| Total Opioid Consumption (OMED) | Part A<br>EXP266<br>(N = 22) | Part A + B | |
|---|---|---|---|
| | | EXP133<br>(N = 81) | BUP50<br>(N = 82) |
| At 48-96 h post-surgery; n | 22 | 81 | 82 |
| Geometric mean | 7.17 | 4.02 | 14.82 |
| % CV | 145.660 | 198.324 | 110.080 |
| Median (Min, max) | 3.75 (0.0, 96.0) | 0.00 (0.0, 75.0) | 22.50 (0.0, 153.0) |
| At 72-96 h post-surgery; n | 22 | 81 | 82 |
| Geometric mean | 3.62 | 1.93 | 4.54 |
| % CV | 137.806 | 218.177 | 142.816 |
| Median (Min, max) | 0.00 (0.0, 43.5) | 0.00 (0.0, 45.0) | 7.50 (0.0, 96.0) |

Abbreviations: CV = coefficient of variation; Max = maximum; Min = minimum; OMED = oral morphine equivalent; SD = standard deviation.
Note: Zero (0) dose is replaced with 3.75 mg to enable geometric mean computation for 0 to 96 h time interval. For other intervals, this 3.75 mg is prorated according to the width of the interval.

FIG. 7 (Cont.)

Table 8 - Analysis of Total Postsurgical Opioid Consumption by Time Interval (Efficacy Analysis Set)

| Total Opioid Consumption (OMED) | EXP133 (N = 81) | BUP50 (N = 82) | p-value[1] | p-value[2] | % Reduction in LSM[3] |
|---|---|---|---|---|---|
| At 0-24 h post-surgery; n | | | | | |
| LSM (95% CI)[4] | 5.50 (4.04, 7.48) | 5.53 (4.06, 7.52) | | | |
| LSM ratio over bupivacaine (95% CI) | 0.99 (0.66, 1.49) | | 0.4897 | 0.9682 | 0.54 |
| At 0-48 h post-surgery; n | | | | | |
| LSM (95% CI)[4] | 11.78 (8.96, 15.49) | 26.76 (20.33, 35.21) | | | |
| LSM ratio from bupivacaine (95% CI) | 0.44 (0.31, 0.63) | | <0.00001 | 0.00002 | 55.98 |
| At 0-72 h post-surgery; n | | | | | |
| LSM (95% CI)[4] | 14.89 (11.50, 19.28) | 38.25 (29.52, 49.55) | | | |
| LSM ratio from bupivacaine (95% CI) | 0.39 (0.28, 0.55) | | <0.00001 | <0.00001 | 61.07 |
| At 0-96 h post-surgery; n | | | | | |
| LSM (95% CI)[4] | 17.68 (13.71, 22.80) | 45.34 (35.14, 58.51) | | | |
| LSM ratio from bupivacaine (95% CI) | 0.39 (0.28, 0.55) | | <0.00001 | <0.00001 | 61.01 |
| At 24-48 h post-surgery; n | | | | | |
| LSM (95% CI)[4] | 4.78 (3.52, 6.48) | 17.73 (13.06, 24.07) | | | |
| LSM ratio from bupivacaine (95% CI) | 0.27 (0.18, 0.40) | | <0.00001 | <0.00001 | 73.04 |
| At 24-72 h post-surgery; n | | | | | |
| LSM (95% CI)[4] | 7.58 (5.77, 9.95) | 29.22 (22.24, 38.39) | | | |
| LSM ratio from bupivacaine (95% CI) | 0.26 (0.18, 0.37) | | <0.00001 | <0.00001 | 74.06 |
| At 24-96 h post-surgery; n | | | | | |
| LSM (95% CI)[4] | 10.07 (7.73, 13.11) | 36.47 (28.00, 47.52) | | | |
| LSM ratio from bupivacaine (95% CI) | 0.28 (0.19, 0.39) | | <0.00001 | <0.00001 | 72.39 |

FIG. 8

Table 8 - Analysis of Total Postsurgical Opioid Consumption by Time Interval (Efficacy Analysis Set)

| Total Opioid Consumption (OMED) | EXP133 (N = 81) | BUP50 (N = 82) | p-value[1] | p-value[2] | % Reduction in LSM[3] |
|---|---|---|---|---|---|
| At 48-72 h post-surgery; n | | | | | |
| LSM (95% CI)[4] | 2.08 (1.55, 2.79) | 8.88 (6.63, 11.91) | | | |
| LSM ratio from bupivacaine (95% CI) | 0.23 (0.16, 0.34) | | <0.00001 | <0.00001 | 76.58 |
| At 48-96 h post-surgery; n | | | | | |
| LSM (95% CI)[4] | 4.46 (3.37, 5.89) | 15.62 (11.81, 20.65) | | | |
| LSM ratio from bupivacaine (95% CI) | 0.29 (0.20, 0.41) | | <0.00001 | <0.00001 | 71.45 |
| At 72-96 h post-surgery; n | | | | | |
| LSM (95% CI)[4] | 2.09 (1.54, 2.84) | 4.77 (3.51, 6.48) | | | |
| LSM ratio from bupivacaine (95% CI) | 0.44 (0.29, 0.66) | | 0.00003 | 0.0001 | 56.18 |

Abbreviations: ANCOVA = analysis of covariance; CI = confidence interval; CMH = Cochran-Mantel-Haenszel; h = hour(s); $H_a$ = alternative hypothesis; LSM = least squares mean; OMED = oral morphine equivalent.
[1] p-value for LSM difference. One-sided test for $H_a$ = mean total opioid consumption for EXPAREL < mean total opioid consumption for bupivacaine HCl.
[2] p-value for CMH test. The 2-sided CMH test for the row mean score difference was calculated using modified ridit scores stratified by pooled investigator site.
[3] Percent reduction was calculated as (LSM for bupivacaine - LSM for EXPAREL)/LSM for bupivacaine x 100%.
[4] From ANCOVA with main effect of treatment and covariates of site (categorical) and age (continuous). Total dose is log-transformed in the analysis and back transformed in the presentation. Note: Zero (0) dose is replaced with 3.75 mg to enable log-transformation.

FIG. 8 (Cont.)

Table 9 - Analysis of Postsurgical Opioid-Free Subjects Through 96 h (Efficacy Analysis Set)

| Time Post-surgery | Part A+B | | |
|---|---|---|---|
| | EXP133 (N = 81) | BUP50 (N = 82) | 95% CI | p-value[1] |
| 0-24 h | | | | |
| Opioid-free (%)[2] | 35.3 | 33.2 | | |
| Not opioid-free (%) | 64.7 | 66.8 | | |
| Odds ratio | 1.10 | | 0.56, 2.16 | 0.3961 |
| At 0-48 h | | | | |
| Opioid-free (%)[2] | 25.1 | 7.5 | | |
| Not opioid-free (%) | 74.9 | 92.5 | | |
| Odds ratio | 4.12 | | 1.75, 9.69 | 0.0006 |
| At 0-72 h | | | | |
| Opioid-free (%)[2] | 24.4 | 6.0 | | |
| Not opioid-free (%) | 75.6 | 94.0 | | |
| Odds ratio | 5.04 | | 2.01, 12.62 | 0.0003 |
| At 0-96 h | | | | |
| Opioid-free (%)[2] | 24.4 | 6.0 | | |
| Not opioid-free (%) | 75.6 | 94.0 | | |
| Odds ratio | 5.04 | | 2.01, 12.62 | 0.0003 |

Abbreviations: CI = confidence interval; h = hour(s); LSM = least squares mean.
1 p-value for $H_a$: opioid-free odds ratio>1.
2 LSM estimate using logistic regression with treatment as main effect, site as categorical and age as continuous covariates.

FIG. 9

Table 10 - Summary of Time to First Opioid Consumption Post-surgery (Efficacy Analysis Set)

| Statistic | Part A<br>EXP266<br>(N = 22) | Part A + B<br>EXP133<br>(N = 81) | Part A + B<br>BUP50<br>(N = 82) |
|---|---|---|---|
| Subjects taking no opioid breakthrough medication, n(%) | 1 (4.5) | 26 (32.1) | 8 (9.8) |
| Subjects taking opioid breakthrough medication, n(%) | 21 (95.5) | 55 (67.9) | 74 (90.2) |
| Time (h) to first rescue medication[1] | | | |
| 25th percentile (95% CI) | 12.32 (0.42, 15.25) | 14.17 (10.58, 16.72) | 17.17 (13.12, 18.10) |
| Median (95% CI) | 16.06 (12.32, 20.57) | 20.27 (17.13, 29.98) | 20.68 (19.28, 24.40) |
| 75th percentile (95% CI) | 22.28 (16.10, 35.53) | NE (36.07, NE) | 32.35 (25.32, 35.37) |
| Min, Max | 0.4, 335.2[2] | 0.2, 412.3[2] | 0.3, 339.3[2] |
| Comparison to bupivacaine | | | |
| Hazard ratio (95% CI) from Cox model[3] | NC | 0.65 (0.45, 0.93) | |
| 1-sided P-value from Cox model | | 0.0089 | |
| 2-sided P-value from log-rank test[4] | | 0.0269 | |

Abbreviations: CI = confidence interval; Max = maximum; Min = minimum; NC = not computed, NE = not evaluable.
[1] Kaplan-Meier estimate.
[2] Mean observation was censored.
[3] Cox proportional hazards model with treatment as main effect and site as categorical and age as continuous covariates.
[4] Log-rank test stratified by site.

FIG. 10

Table 11 - Summary of the Worst and Average Numeric Rating Scale Pain Intensity Scores Over the Last 24 h From Post-surgery Day 1 Through Day 4 (Efficacy Analysis Set)

| Post-surgery Day | Worst Pain | | | | Average Pain | | | |
|---|---|---|---|---|---|---|---|---|
| | Part A | | Part A + B | | Part A | | Part A + B | |
| | EXP266 (N = 22) | EXP133 (N = 81) | EXP133 (N = 81) | BUP50 (N = 82) | EXP266 (N = 22) | EXP133 (N = 81) | EXP133 (N = 81) | BUP50 (N = 82) |
| Day 1; n | 22 | 81 | 81 | 81 | 22 | 81 | 81 | 81 |
| Mean (SD) | 6.0 (3.18) | 4.4 (3.13) | 4.4 (3.13) | 5.3 (3.06) | 4.7 (2.60) | 2.8 (2.32) | 2.8 (2.32) | 3.0 (2.58) |
| Median (Min, max) | 6.0 (0, 10) | 5.0 (0, 10) | 5.0 (0, 10) | 6.0 (0, 10) | 4.0 (1, 10) | 3.0 (0, 8) | 3.0 (0, 8) | 3.0 (0, 8) |
| Day 2; n | 21 | 81 | 81 | 80 | 21 | 81 | 81 | 80 |
| Mean (SD) | 6.1 (2.49) | 4.4 (3.14) | 4.4 (3.14) | 7.3 (2.22) | 3.9 (2.74) | 2.9 (2.33) | 2.9 (2.33) | 4.8 (2.01) |
| Median (Min, max) | 6.0 (2, 10) | 5.0 (0, 10) | 5.0 (0, 10) | 8.0 (0, 10) | 4.0 (0, 8) | 3.0 (0, 9) | 3.0 (0, 9) | 5.0 (0, 8) |
| Day 3; n | 21 | 81 | 81 | 80 | 21 | 81 | 81 | 80 |
| Mean (SD) | 4.3 (3.55) | 2.7 (2.87) | 2.7 (2.87) | 6.1 (2.69) | 3.5 (3.19) | 1.8 (2.05) | 1.8 (2.05) | 4.1 (2.19) |
| Median (Min, max) | 4.0 (0, 10) | 2.0 (0, 10) | 2.0 (0, 10) | 7.0 (0, 10) | 4.0 (0, 8) | 1.0 (0, 8) | 1.0 (0, 8) | 4.5 (0, 8) |
| Day 4; n | 21 | 81 | 81 | 80 | 21 | 81 | 81 | 80 |
| Mean (SD) | 4.4 (3.68) | 2.8 (2.84) | 2.8 (2.84) | 5.1 (2.81) | 3.2 (3.14) | 1.7 (2.03) | 1.7 (2.03) | 3.3 (2.10) |
| Median (Min, max) | 4.0 (0, 10) | 2.0 (0, 10) | 2.0 (0, 10) | 5.5 (0, 10) | 3.0 (0, 8) | 1.0 (0, 8) | 1.0 (0, 8) | 3.0 (0, 9) |

Abbreviations: h = hour(s); Max = maximum; Min = mimimum; SD = standard deviation.

FIG. 11

Table 12 - Analysis of the Worst and Average Numeric Rating Scale Pain Intensity Scores Over the Last 24 h From Post surgery Day 1 Through Day 4 – Parts A + B (Efficacy Analysis Set)

| Post-surgery Day | Worst Pain | | | | Average Pain | | | |
|---|---|---|---|---|---|---|---|---|
| | EXP133 (N = 81) | BUP50 (N = 82) | LSM Diff[1] | p-value[2] | EXP133 (N = 81) | BUP50 (N = 82) | LSM Diff[1] | p-value[2] |
| Day 1 | | | | | | | | |
| LSM (SE)[3] | 5.1 (0.33) | 5.9 (0.34) | -0.8 (0.44) | 0.0296 | 3.1 (0.27) | 3.2 (0.28) | -0.1 (0.36) | 0.3419 |
| 95% CI | 4.4, 5.7 | 5.3, 6.6 | -1.7, 0.0 | | 2.6, 3.6 | 2.7, 3.8 | -0.9, 0.6 | |
| Day 2 | | | | | | | | |
| LSM (SE)[3] | 4.9 (0.30) | 7.7 (0.31) | -2.9 (0.40) | <0.00001 | 3.3 (0.24) | 5.2 (0.24) | -1.9 (0.31) | <0.00001 |
| 95% CI | 4.3, 5.5 | 7.1, 8.3 | -3.6, -2.1 | | 2.8, 3.7 | 4.7, 5.7 | -2.5, -1.3 | |
| Day 3 | | | | | | | | |
| LSM (SE)[3] | 3.1 (0.31) | 6.4 (0.32) | -3.3 (0.41) | <0.00001 | 2.0 (0.24) | 4.2 (0.24) | -2.2 (0.31) | <0.00001 |
| 95% CI | 2.5, 3.7 | 5.7, 7.0 | -4.1, -2.5 | | 1.6, 2.5 | 3.7, 4.7 | -2.8, -1.6 | |
| Day 4 | | | | | | | | |
| LSM (SE)[3] | 3.1 (0.32) | 5.2 (0.33) | -2.1 (0.43) | <0.00001 | 1.9, (0.23) | 3.4 (0.24) | -1.5 (0.31) | <0.00001 |
| 95% CI | 2.4, 3.7 | 4.6, 5.9 | -3.0, -1.3 | | 1.5, 2.4 | 3.0, 3.9 | -2.1, -0.9 | |

Abbreviations: ANCOVA = analysis of covariance; CI = confidence interval; Diff = difference; h = hour(s); $H_a$ = alternative hypothesis; LSM = least squares mean; Max = maximum; Min = minimum; SD = standard deviation; SE = standard error.
1 Difference from bupivacaine.
2 1-sided p-value for LSM difference. One-sided test for $H_a$ = mean pain intensity score for EXPAREL < mean pain intensity score for bupivacaine HCl.
3 From ANCOVA with main effect of treatment, categorical covariate of pooled investigator site, and continuous covariate of age.

FIG. 12

| Table 13 – Summary of Pharmacokinetic Parameters (PK Parameter Analysis Set) | | | |
|---|---|---|---|
| | EXP266 (N = 22) | EXP133 (N = 22) | BUP50 (N = 21) |
| $AUC_{0-last}$ (h × ng/mL); n | 21 | 21 | 21 |
| Geometric mean (%CV) | 22667.28 (33.2) | 14517.81 (42.1) | 8151.07 (35.3) |
| Mean (SD) | 23795.07 (7899.464) | 16004.95 (6740.052) | 8791.20 (3105.844) |
| Median (Min, Max) | 23041.11 (11296.3, 46826.0) | 18018.56 (5467.3, 26288.7) | 8731.67 (2475.3, 15100.0) |
| Dose-normalized $AUC_{0-last}$ [(h × ng/mL)/(mg)]; n | 21 | 21 | 21 |
| Geometric mean (%CV) | 63.9055 (33.1979) | 65.4840 (42.1123) | 61.2863 (35.3290) |
| Mean (SD) | 67.0850 (22.2708) | 72.1919 (30.4017) | 66.0993 (23.3522) |
| Median (Min, Max) | 64.9594 (31.8476, 132.0157) | 81.2745 (24.6608, 118.5779) | 65.6516 (18.6115, 113.5342) |
| $AUC_{0-\infty}$ (h × ng/mL); n | 19 | 20 | 21 |
| Geometric mean (%CV) | 24316.19 (38.5) | 15353.48 (42.4) | 8282.33 (36.9) |
| Mean (SD) | 25919.65 (9966.132) | 17004.02 (7206.041) | 8961.00 (3310.925) |
| Median (Min, Max) | 23344.19 (11990.3, 51543.1) | 18797.85 (5629.7, 28107.0) | 8819.27 (2535.5, 16958.6) |
| Dose-normalized $AUC_{0-\infty}$ [(h × ng/mL)/(mg)]; n | 19 | 20 | 21 |
| Geometric mean (%CV) | 68.5543 (38.4501) | 69.2534 (42.3785) | 62.2732 (36.9482) |
| Mean (SD) | 73.0749 (28.0974) | 76.6983 (32.5036) | 67.3759 (24.8942) |
| Median (Min, Max) | 65.8139 (33.8042, 145.3145) | 84.7896 (25.3935, 126.7795) | 66.3103 (19.0641, 127.5083) |
| $AUC_{extr}$ (%); n | 20 | 21 | 21 |
| Geometric mean (%CV) | 4.46 (104.3) | 2.35 (128.6) | 0.92 (147.3) |
| Mean (SD) | 8.33 (8.691) | 4.47 (5.742) | 1.56 (2.295) |
| Median (Min, Max) | 5.53 (0.2, 29.8) | 2.07 (0.2, 22.4) | 0.98 (0.2, 11.0) |
| $C_{max}$ (ng/mL); n | NA | NA | 21 |
| Geometric mean (%CV) | NA | NA | 405.63 (50.8) |
| Mean (SD) | NA | NA | 462.38 (235.117) |
| Median (Min, Max) | NA | NA | 413.00 (123.0, 967.0) |
| Dose-normalized $C_{max}$ [(ng/mL)/(mg)]; n | NA | NA | 21 |
| Geometric mean (%CV) | NA | NA | 3.0499 (50.8492) |
| Mean (SD) | NA | NA | 3.4765 (1.7678) |
| Median (Min, Max) | NA | NA | 3.1053 (0.9248, 7.2707) |

FIG. 14

| Table 13 – Summary of Pharmacokinetic Parameters (PK Parameter Analysis Set) | | | |
|---|---|---|---|
| | EXP266 (N = 22) | EXP133 (N = 22) | BUP50 (N = 21) |
| Early $C_{max}$ (ng/mL); n | 21 | 21 | NA |
|   Geometric mean (%CV) | 340.22 (40.0) | 330.96 (63.1) | NA |
|   Mean (SD) | 363.43 (145.305) | 381.62 (240.733) | NA |
|   Median (Min, Max) | 349.00 (173.0, 791.0) | 312.00 (162.0, 1220.0) | NA |
| Dose-normalized early $C_{max}$ [(ng/mL)/(mg)]; n | 21 | 21 | NA |
|   Geometric mean (%CV) | 0.9592 (39.9816) | 1.4928 (63.0821) | NA |
|   Mean (SD) | 1.0246 (0.4097) | 1.7213 (1.0859) | NA |
|   Median (Min, Max) | 0.9839 (0.4877, 2.2301) | 1.4073 (0.7307, 5.5029) | NA |
| Late $C_{max}$ (ng/mL); n | 21 | 21 | NA |
|   Geometric mean (%CV) | 191.50 (34.1) | 95.17 (52.4) | NA |
|   Mean (SD) | 203.74 (69.493) | 106.56 (55.824) | NA |
|   Median (Min, Max) | 214.00 (81.6, 361.0) | 93.20 (28.1, 305.0) | NA |
| Dose-normalized late $C_{max}$ [(ng/mL)/(mg)]; n | 21 | 21 | NA |
|   Geometric mean (%CV) | 0.5399 (34.1082) | 0.4293 (52.3862) | NA |
|   Mean (SD) | 0.5744 (0.1959) | 0.4807 (0.2518) | NA |
|   Median (Min, Max) | 0.6033 (0.2301, 1.0178) | 0.4204 (0.1267, 1.3757) | NA |
| $T_{max}$ (h); n | NA | NA | 21 |
|   Median (Min, Max) | NA | NA | 2.28 (1.7, 8.2) |
| Early $T_{max}$ (h); n | 21 | 21 | NA |
|   Median (Min, Max) | 8.00 (1.7, 24.3) | 8.05 (1.7, 11.7) | NA |
| Late $T_{max}$ (h); n | 21 | 21 | NA |
|   Median (Min, Max) | 84.92 (48.0, 120.0) | 72.32 (48.0, 96.5) | NA |
| $t_{1/2el}$ (h) | 20 | 20 | 21 |
|   Geometric mean (%CV) | 29.39 (61.9) | 25.21 (51.1) | 13.18 (27.9) |
|   Mean (SD) | 34.03 (21.067) | 28.02 (14.307) | 13.75 |
|   Median (Min, Max) | 26.65 (12.3, 95.3) | 22.53 (10.9, 68.3) | 13.91 (6.2, 20.0) |
| CL/F (L/h) | 19 | 20 | 21 |
|   Geometric mean (%CV) | 14.59 (35.7) | 14.44 (53.4) | 16.06 (57.1) |
|   Mean (SD) | 15.50 (5.538) | 16.26 (8.688) | 17.86 (10.196) |
|   Median (Min, Max) | 15.19 (6.9, 29.6) | 11.80 (7.9, 39.4) | 15.08 (7.8, 52.5) |

FIG. 14 (Cont. 1)

| Table 13 – Summary of Pharmacokinetic Parameters (PK Parameter Analysis Set) | | | |
|---|---|---|---|
| | EXP266 (N = 22) | EXP133 (N = 22) | BUP50 (N = 21) |
| $V_d/F$ (L) | 19 | 20 | 21 |
| Geometric mean (%CV) | 581.42 (44.4) | 525.11 (58.8) | 305.31 (65.2) |
| Mean (SD) | 639.86 (283.874) | 604.22 (355.541) | 359.23 (234.215) |
| Median (Min, Max) | 609.27 (268.2, 1110.2) | 462.97 (277.4, 1389.8) | 316.67 (94.2, 1019.2) |

Abbreviations: AUC = area under the curve; AUC0-∞ = area under the curve from the time of dosing to infinity; AUC0-last = area under the curve from the time of dosing to the of the last quantifiable concentration; AUCextr = extrapolated area under the curve from time of last point above lower limit of quantification to infinity; CL/F = apparent clearance; Cmax = maximum plasma concentration; CV = coefficient of variation; h = hour; Max = maximum; Min = minimum; PK = pharmacokinetic; SD = standard deviation; t1/2el = apparent terminal elimination half-life; Tmax = time of maximum plasma concentration; Vd/F = apparent volume of distribution.

FIG. 14 (Cont. 2)

Table 14.2-14
Summary of PK Concentration (ng/mL) by Time Point
PKC Analysis Set

| Time Point | Statistic | EXPAREL 226mg (N=22) | EXPAREL 133mg (N=22) | Bupivacaine HCl (N=22) |
|---|---|---|---|---|
| Pre-dose | n | 22 | 21 | 22 |
| | Geometric Mean | 0.00 | 0.00 | 0.00 |
| | %CV | 469.0 | NC | 469.0 |
| | Mean | 0.07 | 0.00 | 0.14 |
| | SD | 0.313 | 0.000 | 0.676 |
| | Median | 0.00 | 0.00 | 0.00 |
| | Min, Max | 0.0, 1.5 | 0.0, 0.0 | 0.0, 3.2 |
| 0.5 hrs | n | 22 | 19 | 21 |
| | Geometric Mean | 0.00 | 35.11 | 80.88 |
| | %CV | 76.0 | 65.7 | 45.5 |
| | Mean | 54.43 | 41.03 | 89.79 |
| | SD | 41.371 | 26.977 | 40.817 |
| | Median | 45.00 | 35.80 | 79.20 |
| | Min, Max | 0.0, 157.0 | 14.2, 127.0 | 25.0, 166.0 |
| 0.75 hrs | n | 22 | 20 | 21 |
| | Geometric Mean | 45.60 | 33.59 | 84.39 |
| | %CV | 65.8 | 62.7 | 44.4 |
| | Mean | 56.71 | 38.70 | 94.33 |
| | SD | 37.315 | 24.247 | 41.916 |
| | Median | 47.20 | 32.50 | 85.80 |
| | Min, Max | 7.8, 145.0 | 13.1, 122.0 | 18.5, 173.0 |

CV = coefficient of variation; SD = standard deviation; NC = Not calculable. Subject 401-0143 is excluded from the table summaries because her predose PK concentration is >5% of Cmax.

FIG. 14 (Cont. 3)

Table 14.2-14
Summary of PK Concentration (ng/mL) by Time Point
PKC Analysis Set

| Time Point | Statistic | EXPAREL 226mg (N=22) | EXPAREL 133mg (N=22) | Bupivacaine HCl (N=22) |
|---|---|---|---|---|
| 1 hrs | n | 22 | 20 | 22 |
| | Geometric Mean | 44.17 | 34.03 | 87.56 |
| | %CV | 65.2 | 102.1 | 68.8 |
| | Mean | 54.88 | 44.91 | 104.25 |
| | SD | 35.761 | 45.855 | 71.719 |
| | Median | 45.00 | 31.65 | 78.75 |
| | Min, Max | 7.7, 138.0 | 12.7, 219.0 | 23.4, 346.0 |
| 2 hrs | n | 22 | 19 | 21 |
| | Geometric Mean | 152.67 | 142.89 | 280.92 |
| | %CV | 97.9 | 113.6 | 71.8 |
| | Mean | 289.75 | 264.70 | 404.31 |
| | SD | 283.786 | 300.824 | 290.215 |
| | Median | 226.50 | 151.00 | 413.00 |
| | Min, Max | 7.6, 1100.0 | 23.9, 1220.0 | 38.2, 967.0 |
| 8 hrs | n | 21 | 21 | 21 |
| | Geometric Mean | 274.92 | 292.51 | 260.75 |
| | %CV | 30.9 | 44.2 | 37.8 |
| | Mean | 286.71 | 321.86 | 281.91 |
| | SD | 88.481 | 142.378 | 106.540 |
| | Median | 274.00 | 288.00 | 283.00 |
| | Min, Max | 158.0, 546.0 | 136.0, 646.0 | 86.1, 541.0 |

CV = coefficient of variation; SD = standard deviation; NC = Not calculable. Subject 401-0143 is excluded from the table summaries because her predose PK concentration is >5% of Cmax.

FIG. 14 (Cont. 4)

Table 14.2-14
Summary of PK Concentration (ng/mL) by Time Point
PKC Analysis Set

| Time Point | Statistic | EXPAREL 226mg (N=22) | EXPAREL 133mg (N=22) | Bupivacaine HCl (N=22) |
|---|---|---|---|---|
| 12 hrs | n | 22 | 21 | 21 |
| | Geometric Mean | 248.65 | 238.10 | 198.30 |
| | %CV | 26.4 | 49.0 | 47.8 |
| | Mean | 256.50 | 272.39 | 221.88 |
| | SD | 67.822 | 133.502 | 106.024 |
| | Median | 259.00 | 272.00 | 223.00 |
| | Min, Max | 170.0, 459.0 | 68.4, 563.0 | 51.4, 545.0 |
| 24 hrs | n | 22 | 21 | 21 |
| | Geometric Mean | 171.89 | 175.38 | 135.78 |
| | %CV | 45.9 | 47.5 | 45.1 |
| | Mean | 189.54 | 199.54 | 152.30 |
| | SD | 87.085 | 94.867 | 68.754 |
| | Median | 176.00 | 221.00 | 153.00 |
| | Min, Max | 69.1, 412.0 | 65.8, 344.0 | 25.4, 355.0 |
| 30 hrs | n | 21 | 21 | 21 |
| | Geometric Mean | 143.19 | 122.12 | 103.92 |
| | %CV | 48.6 | 58.2 | 41.4 |
| | Mean | 159.46 | 150.40 | 114.39 |
| | SD | 77.430 | 87.533 | 47.380 |
| | Median | 147.00 | 131.00 | 107.00 |
| | Min, Max | 50.8, 377.0 | 28.7, 275.0 | 25.0, 230.0 |

CV = coefficient of variation; SD = standard deviation; NC = Not calculable. Subject 401-0143 is excluded from the table summaries because her predose PK concentration is >5% of Cmax.

FIG. 14 (Cont. 5)

Table 14.2-14
Summary of PK Concentration (ng/mL) by Time Point
PKC Analysis Set

| Time Point | Statistic | EXPAREL 226mg (N=22) | EXPAREL 133mg (N=22) | Bupivacaine HCl (N=22) |
|---|---|---|---|---|
| 48 hrs | n | 20 | 21 | 20 |
| | Geometric Mean | 131.43 | 89.80 | 44.87 |
| | %CV | 54.8 | 61.9 | 46.8 |
| | Mean | 150.44 | 110.70 | 51.56 |
| | SD | 82.424 | 68.541 | 24.109 |
| | Median | 130.00 | 109.00 | 51.50 |
| | Min, Max | 46.1, 349.0 | 14.1, 305.0 | 8.2, 94.5 |
| 60 hrs | n | 21 | 21 | 19 |
| | Geometric Mean | 148.67 | 83.14 | 28.28 |
| | %CV | 44.5 | 54.5 | 51.1 |
| | Mean | 164.37 | 97.64 | 34.19 |
| | SD | 73.129 | 53.220 | 17.487 |
| | Median | 147.00 | 102.00 | 36.80 |
| | Min, Max | 56.8, 310.0 | 12.0, 262.0 | 3.5, 69.3 |
| 72 hrs | n | 21 | 21 | 19 |
| | Geometric Mean | 169.06 | 85.08 | 20.32 |
| | %CV | 38.5 | 44.6 | 48.7 |
| | Mean | 181.79 | 96.10 | 23.04 |
| | SD | 70.076 | 42.826 | 11.227 |
| | Median | 190.00 | 93.20 | 21.00 |
| | Min, Max | 78.2, 361.0 | 19.7, 191.0 | 6.7, 45.1 |

CV = coefficient of variation; SD = standard deviation; NC = Not calculable. Subject 401-0143 is excluded from the table summaries because her predose PK concentration is >5% of Cmax.

FIG. 14 (Cont. 6)

Table 14.2-14
Summary of PK Concentration (ng/mL) by Time Point
PKC Analysis Set

| Time Point | Statistic | EXPAREL 226mg (N=22) | EXPAREL 133mg (N=22) | Bupivacaine HCl (N=22) |
|---|---|---|---|---|
| 84 hrs | n | 20 | 21 | 19 |
|  | Geometric Mean | 152.74 | 72.55 | 10.60 |
|  | %CV | 35.1 | 36.7 | 62.4 |
|  | Mean | 162.34 | 79.02 | 13.38 |
|  | SD | 56.965 | 29.031 | 8.340 |
|  | Median | 154.50 | 82.60 | 11.40 |
|  | Min, Max | 78.8, 272.0 | 17.5, 133.0 | 1.6, 30.9 |
| 96 hrs | n | 21 | 21 | 15 |
|  | Geometric Mean | 155.94 | 66.78 | 6.69 |
|  | %CV | 37.0 | 37.1 | 64.5 |
|  | Mean | 166.88 | 72.15 | 7.83 |
|  | SD | 61.661 | 26.776 | 5.053 |
|  | Median | 163.00 | 74.70 | 5.60 |
|  | Min, Max | 81.6, 303.0 | 27.8, 131.0 | 3.4, 20.9 |
| 120 hrs | n | 21 | 21 | 8 |
|  | Geometric Mean | 97.49 | 37.72 | 2.56 |
|  | %CV | 48.7 | 46.7 | 76.2 |
|  | Mean | 111.81 | 42.61 | 3.21 |
|  | SD | 54.420 | 19.892 | 2.446 |
|  | Median | 108.00 | 42.10 | 1.86 |
|  | Min, Max | 22.5, 222.0 | 6.9, 101.0 | 1.3, 7.9 |

CV = coefficient of variation; SD = standard deviation; NC = Not calculable. Subject 401-0143 is excluded from the table summaries because her predose PK concentration is >5% of Cmax.

FIG. 14 (Cont. 7)

Table 14.2-14
Summary of PK Concentration (ng/mL) by Time Point
PKC Analysis Set

| Time Point | Statistic | EXPAREL 226mg (N=22) | EXPAREL 133mg (N=22) | Bupivacaine HCl (N=22) |
|---|---|---|---|---|
| 144 hrs | n | 21 | 21 | 1 |
| | Geometric Mean | 41.82 | 18.40 | 2.01 |
| | %CV | 69.5 | 64.1 | NC |
| | Mean | 64.61 | 23.26 | 2.01 |
| | SD | 44.896 | 14.910 | NC |
| | Median | 59.30 | 21.20 | 2.01 |
| | Min, Max | 0.5, 167.0 | 1.9, 64.1 | 2.0, 2.0 |
| 168 hrs | n | 21 | 19 | 0 |
| | Geometric Mean | 28.66 | 9.56 | |
| | %CV | 87.2 | 72.0 | |
| | Mean | 44.53 | 12.25 | |
| | SD | 38.835 | 8.822 | |
| | Median | 30.90 | 9.22 | |
| | Min, Max | 1.6, 141.0 | 1.1, 35.7 | |

CV = coefficient of variation; SD = standard deviation; NC = Not calculable. Subject 401-0143 is excluded from the table summaries because her predose PK concentration is >5% of Cmax.

FIG. 14 (Cont. 8)

Table 14.2-15
Summary of PK Dose-Normalized Parameters
PKP Analysis Set

| Parameter | Statistic | EXPAREL 226mg (N=22) | EXPAREL 133mg (N=22) | Bupivacaine HCl (N=21) |
|---|---|---|---|---|
| AUC$_{0-last}$/Dose [(hr*ng/mL)/(mg)] | n | 21 | 21 | 21 |
| | Geometric Mean | 63.9055 | 65.4840 | 61.2863 |
| | %CV | 33.1979 | 42.1123 | 35.3290 |
| | Mean | 67.0850 | 72.1919 | 66.0993 |
| | SD | 22.2708 | 30.4017 | 23.3522 |
| | Median | 64.9594 | 81.2745 | 65.6516 |
| | Min, Max | 31.8476, 132.0157 | 24.6608, 118.5779 | 18.6115, 113.5342 |
| AUC$_{0-\infty}$/Dose [(hr*ng/mL)/(mg)] | n | 19 | 20 | 21 |
| | Geometric Mean | 68.5543 | 69.2534 | 62.2732 |
| | %CV | 38.4501 | 42.3785 | 36.9482 |
| | Mean | 73.0749 | 76.6983 | 67.3759 |
| | SD | 28.0974 | 32.5036 | 24.8942 |
| | Median | 65.8139 | 84.7896 | 66.3103 |
| | Min, Max | 33.8042, 145.3145 | 25.3935, 126.7795 | 19.0641, 127.5083 |

CV = coefficient of variation; SD = standard deviation.
Subjects 401-0013 (EXPAREL 133mg), 401-0018 (EXPAREL 266mg) have Adjusted R-square <0.80. Their AUC(0-inf), t1/2, CL/F, and Vd/F are excluded from the summaries.
Subject 402-0115 (EXPAREL 266mg) has AUC%Extrap >30%. Her AUC$_{0-inf}$, AUC%Extrap, CL/F and Vd/F are excluded from the summaries.
Subject 404-0077 is excluded from the table because her PK sample collection was stopped after 24-hour time point.
Subject 401-0143 is excluded from the table summaries because her predose PK concentration is >5% of C$_{max}$.

FIG. 14 (Cont. 9)

Table 14.2-15 Summary of PK Dose-Normalized Parameters PKP Analysis Set

| Parameter | Statistic | EXPAREL 226mg (N=22) | EXPAREL 133mg (N=22) | Bupivacaine HCl (N=21) |
|---|---|---|---|---|
| $C_{max}$/Dose [(ng/mL)/(mg)] | n | | | 21 |
| | Geometric Mean | | | 3.0499 |
| | %CV | | | 50.8492 |
| | Mean | | | 3.4765 |
| | SD | | | 1.7678 |
| | Median | | | 3.1053 |
| | Min, Max | | | 0.9248, 7.2707 |
| Early $C_{max}$/ Dose [(ng/mL)/ (mg)] | n | 21 | 21 | |
| | Geometric Mean | 0.9592 | 1.4928 | |
| | %CV | 39.9816 | 63.0821 | |
| | Mean | 1.0246 | 1.7213 | |
| | SD | 0.4097 | 1.0859 | |
| | Median | 0.9839 | 1.4073 | |
| | Min, Max | 0.4877, 2.2301 | 0.7307, 5.5029 | |
| Late $C_{max}$/ Dose [(ng/mL)/ (mg)] | n | 21 | 21 | |
| | Geometric Mean | 0.5399 | 0.4293 | |
| | %CV | 34.1082 | 52.3862 | |
| | Mean | 0.5744 | 0.4807 | |
| | SD | 0.1959 | 0.2518 | |
| | Median | 0.6033 | 0.4204 | |
| | Min, Max | 0.2301, 1.0178 | 0.1267, 1.3757 | |

CV = coefficient of variation; SD = standard deviation.
Subjects 401-0013 (EXPAREL 133mg), 401-0018 (EXPAREL 266mg) have Adjusted R-square <0.80. Their AUC(0-inf), t1/2, CL/F, and Vd/F are excluded from the summaries.
Subject 402-0115 (EXPAREL 266mg) has AUC%Extrap >30%. Her $AUC_{0-inf}$, AUC%Extrap, CL/F and Vd/F are excluded from the summaries.
Subject 404-0077 is excluded from the table because her PK sample collection was stopped after 24-hour time point.
Subject 401-0143 is excluded from the table summaries because her predose PK concentration is >5% of $C_{max}$.

FIG. 14 (Cont. 10)

Table 14 - Summary of Time to Onset and Duration of Motor and Sensory Block (PD Analysis Set)

| | EXP266 (N = 22) | EXP133 (N = 22) | BUP50 (N = 22) |
|---|---|---|---|
| Number of subjects with motor block, n (%) | | | |
| Onset observed | 13 (59.1) | 8 (36.4) | 9 (40.9) |
| Onset censored | 9 (40.9) | 14 (63.6) | 13 (59.1) |
| Time (h) to onset of motor block[1] | | | |
| 25th percentile (95% CI) | 0.48 (0.23, 0.73) | 0.73 (0.27, NE) | 0.50 (0.22, 0.98) |
| Median (95% CI) | 0.78 (0.48, NE) | NE (0.73, NE) | NE (0.50, NE) |
| 75th percentile (95% CI) | NE (0.80, NE) | NE (NE, NE) | NE (0.98, NE) |
| Min, max | 0.2, 1.8[2] | 0.3, 1.5[2] | 0.2, 1.6[2] |
| Duration (h) of motor block[1] | | | |
| 25th percentile (95% CI) | 22.95 (7.50, 47.20) | 22.48 (7.20, 47.87) | 24.23 (9.92, 83.22) |
| Median (95% CI) | 47.47 (22.95, 83.33) | 47.87 (11.37, NE) | 83.22 (24.02, 142.58) |
| 75th percentile (95% CI) | 83.33 (47.20, NE) | 96.15 (23.45, NE) | 142.58 (29.53, NE) |
| Min, max | 0.8[2], 95.7 | 0.5[2], 143.4 | 0.6[2], 166.7[2] |
| Comparison to bupivacaine in duration of motor block | | | |
| Cox proportional model harzards ratio (95% CI)[3] | 2.01 (0.80, 5.08) | 1.59 (0.55, 4.56) | |
| 1-sided p-value from Cox model | 0.9310 | 0.8034 | |
| 2-sided p-value from log-rank test | 0.1347 | 0.4355 | |
| Number of subjects with sensory block, n (%) | | | |
| Onset observed | 13 (59.1) | 10 (45.5) | 14 (63.6) |
| Onset censored | 9 (4.9) | 12 (54.5) | 8 (36.4) |

FIG. 15

Table 15 - Overview of Treatment-emergent Adverse Events (Safety Analysis Set)

| | Part A | Part A+B | |
|---|---|---|---|
| | EXP266 (N=22) n (%) | EXP133 (N=81) n (%) | BUP50 (N=82) n (%) |
| Subjects with any TEAE | 13 (59.1) | 42 (51.9) | 45 (54.9) |
| Max severity of mild | 7 (31.8) | 32 (39.5) | 35 (42.7) |
| Max severity of moderate | 6 (27.3) | 10 (12.3) | 10 (12.2) |
| Max severity of severe | 0 | 0 | 0 |
| Subjects with ≥1 related TEAE | 4 (18.2) | 5 (6.2) | 2 (2.4) |
| Subjects with ≥1 SAE | 1 (4.5) | 0 | 1 (1.2) |
| Subjects with ≥1 AESI | 0 | 3 (3.7) | 4 (4.9) |
| Subjects that discontinued due to a TEAE | 0 | 0 | 0 |
| Deaths during the study | 0 | 0 | 0 |

Abbreviations: AESI = adverse event of special interest; Max=maximum, TEAE = treatment-emergent adverse event; SAE = serious adverse event.

FIG. 18

Table 16 - Summary of Treatment-emergent Adverse Events Occurring in ≥5% of Subjects in Any Treatment Arm (Safety Analysis Set)

| System Organ Class Preferred Term | Part A EXP266 (N=22) n (%) | Part A+B EXP133 (N=81) n (%) | Part A+B BUP50 (N=82) n (%) |
|---|---|---|---|
| Subjects with ≥1 TEAE | 13 (59.1) | 42 (51.9) | 45 (54.9) |
| Gastrointestinal disorders | 10 (45.5) | 26 (32.1) | 26 (31.7) |
| Nausea | 9 (40.9) | 13 (16.0) | 19 (23.2) |
| Constipation | 3 (13.6) | 10 (12.3) | 16 (19.5) |
| Vomiting | 5 (22.7) | 4 (4.9) | 7 (8.5) |
| Nervous system disorders | 2 (9.1) | 13 (16.0) | 9 (11.0) |
| Headache | 1 (4.5) | 8 (9.9) | 4 (4.9) |
| Skin and subcutaneous tissue disorders | 2 (9.1) | 7 (8.6) | 6 (7.3) |
| Pruritus | 1 (4.5) | 6 (7.4) | 5 (6.1) |

Abbreviations: MedDRA = Medical Dictionary for Regulatory Activities; TEAE = treatment-emergent adverse event.
Adverse events were coded using MedDRA version 25.0.
Subjects that experienced the same TEAE more than once were counted only once at each summary level.

FIG. 19

TREATMENT OF POST-OPERATIVE PAIN VIA SCIATIC NERVE BLOCK WITH SUSTAINED-RELEASE LIPOSOMAL ANESTHETIC COMPOSITIONS

CROSS-REFERENCE TO RELATED APPLICATIONS

This application claims the benefit of U.S. Provisional Application No. 63/422,182, filed Nov. 3, 2022, which is incorporated by reference herein in its entirety.

BACKGROUND

Postsurgical pain is one of the most common forms of acute pain, which is the normal physiological response to tissue insult or injury and has adaptive value by serving as a warning of danger or damage. Most acute pain is either treatable or avoidable, especially when it occurs in a clinical setting. However, if acute pain is poorly or inappropriately treated, it may progress to chronic pain. Thus, effective postsurgical pain control is a critical element in patient recovery following surgery, as the majority of patients may experience significant pain, particularly in the first few days. Improved postsurgical pain management contributes to better healing, faster patient mobilization, shortened hospital stays, and reduced healthcare costs.

Bunionectomy is often used to manage pain in the foot from bunions. Opioids are commonly used to manage postoperative orthopedic pain. Opioid use carries a risk of developing tolerance and dependence. Thus, one goal following surgery is to improve analgesia while reducing opioid consumption.

Multimodal pain management approaches are recommended by professional societies to improve analgesia, reduce opioid use, and decrease opioid-related adverse events (AEs) following knee surgery. It is recommended that protocols include long-acting neuraxial opioids together with scheduled acetaminophen and nonsteroidal anti-inflammatory drugs (NSAIDs). However, many orthopedic pain patients still request opioids after cesarean delivery for breakthrough pain. Thus, there continues to be a need for methods of treating pain associated with surgery, including knee surgery in a subject.

SUMMARY

Provided herein are methods of administering to a peroneal and a tibial nerve of a patient a pharmaceutical composition for post-operative analgesia, comprising: (a) selecting an entry point of an injection needle in a leg of a patient; (b) inserting the injection needle into the patient at the entry point; (c) administering to a sciatic nerve of the patient via the injection needle saline and a pharmaceutical composition; wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the peroneal and the tibial nerve of the patient the pharmaceutical composition for post-operative analgesia.

Provided herein are methods of administering to a peroneal and a tibial nerve of a human patient a pharmaceutical composition for post-operative analgesia, comprising: (a) selecting an entry point of an injection needle in a leg in a patient; (b) advancing a needle tip of the injection needle within a region where the sciatic nerve splits into the peroneal and tibial nerves of the patient along a trajectory that extends between the entry point and where the sciatic nerve splits into the peroneal and tibial nerves; (c) administering to said region through the injection needle saline and a therapeutically effective amount of a pharmaceutical composition; wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the peroneal and the tibial nerve of the human patient the pharmaceutical composition for post-operative analgesia.

Provided herein are methods of treating post-operative foot pain in a patient, comprising: (a) selecting an entry point of an injection needle in a leg of the patient; (b) inserting the injection needle into the leg of the patient at the entry point; (c) administering to the patient saline and a pharmaceutical composition within a sciatic nerve sheath; wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby treating post-operative foot pain in the patient.

Provided herein are methods of administering a peroneal and a tibial nerve block to a patient to reduce post-operative foot pain, comprising: (a) selecting an entry point of an injection needle in a leg of a patient, wherein the entry point comprises the lateral thigh; (b) advancing a needle tip of the injection needle within a region where the sciatic nerve splits into the peroneal and tibial nerves of the patient along a trajectory that extends between the entry point and the region where the sciatic nerve splits into the peroneal and tibial nerves; (c) piercing with the needle tip of the injection needle the sciatic nerve sheath in said region; (d) administering through the injection needle saline and a therapeutically effective amount of a multivesicular liposome pharmaceutical composition; wherein the multivesicular liposome pharmaceutical composition comprises: bupivacaine or a salt thereof; phosphoric acid; a lipid component comprising at least one amphipathic lipid and at least one neutral lipid lacking a hydrophilic head group; and, optionally, a cholesterol and/or a plant sterol, thereby administering a peroneal and the tibial nerve block to the patient.

Further, in some embodiments, the injection needle is connected to a peripheral nerve stimulator (PNS). In some embodiments, the PNS is tuned to 2 hertz and between 0.5 to 1.0 mA. In some embodiments, the PNS is used to identify the region where the sciatic nerve splits into the peroneal and tibial nerves. In some embodiments, selecting the entry point of the injection needle comprises the lateral thigh. In some embodiments, the injection needle is a 100 mm, 21-gauge needle. In some embodiments, the injection needle is insulated. In some embodiments, inserting the injection needle into the leg of the patient comprises advancing a needle tip of the injection needle a region where the sciatic nerve splits into the peroneal and tibial nerves of the patient along a trajectory that extends between the entry point and the region where the sciatic nerve splits into the peroneal and tibial nerves. In some embodiments, the insertion of the injection needle into the leg of the patient comprises piercing the sciatic nerve sheath. In some embodiments, the saline injection comprises no more than 1 to 2 mL of saline. In some embodiments, a syringe used for the saline injection is different from a syringe used for the pharmaceutical administration. In some embodiments, the method comprises administering about 30 mL of the pharmaceutical composition. In some embodiments, the multivesicular liposomes comprise: bupivacaine or a salt thereof; phosphoric acid; a lipid component comprising at least one amphipathic lipid and at least one neutral lipid lacking a hydrophilic head group; and, optionally, a cholesterol and/or a plant sterol, wherein said multivesicular liposomes are made by a process comprising: (a) preparing a first aqueous component comprising phosphoric acid; (b) preparing a lipid component comprising at least one organic solvent, at least one amphipathic lipid, and at least one neutral lipid lacking a hydrophilic head group; (c) mixing said first aqueous component and said lipid component to form a water-in-oil emulsion, wherein at least one component comprises bupivacaine or a salt thereof; (d) mixing said water-in-oil emulsion with a second aqueous component to form solvent spherules; and (e) removing the organic solvent from the solvent spherules to form multivesicular liposomes encapsulating bupivacaine phosphate. In some embodiments, the methods further comprise administering a Mayo Field Block encircling the entire metatarsal bone. In some embodiments, the Mayo Field Block comprises bupivacaine HCl.

BRIEF DESCRIPTION OF THE DRAWINGS

FIG. 1 shows Table 1, a summary of the assessments performed in clinical trial #1.

FIG. 2 shows Table 2, a summary of the pharmacokinetic and pharmacodynamics assessments of clinical trial #1.

FIG. 3 shows Table 3, a summary of the demographics of the participants of clinical trial #1.

FIG. 4 shows Table 4, a summary of the baseline characteristics of the participants of clinical trial #1.

FIG. 5 shows Table 5, a summary of the area under the curve (AUC) of the numeric rating scale (NRS) pain intensity score at 0-96 hours post-surgery for participants in clinical trial #1.

FIG. 6 shows Table 6, a summary of the AUC of NRS pain intensity by time interval for participants in clinical trial #1.

FIG. 7 shows Table 7, a summary of total opioid consumption by time interval for participants in clinical trial #1.

FIG. 8 shows Table 8, a summary of total post-surgical opioid consumption by time interval for participants in clinical trial #1.

FIG. 9 shows Table 9, a summary of post-surgical opioid-free subjects through 96 hours for participants in clinical trial #1.

FIG. 10 shows Table 10, a summary of time to first opioid consumption post-surgery for participants in clinical trial #1.

FIG. 11 shows Table 11, a summary of the worst and average numeric rating scale pain intensity scores over the last 24 hour from post-surgery day 1 through day 4.

FIG. 12 shows Table 12, a summary of the worst and average numeric rating scale pain intensity scores over the last 24 hour from post-surgery day 1 through day 4 for Parts A+B.

FIG. 14 shows Table 13, a summary of the pharmacokinetic parameters.

FIG. 15 shows Table 14, a summary of the time to onset and duration of motor and sensory block for participants in clinical trial #1.

FIG. 18 shows Table 15, a summary of treatment-emergent adverse events for participants in clinical trial #1.

FIG. 19 shows Table 16, a summary of treatment-emergent adverse events occurring in ≥5% of subjects in any treatment arm.

DETAILED DESCRIPTION

Figure 13:
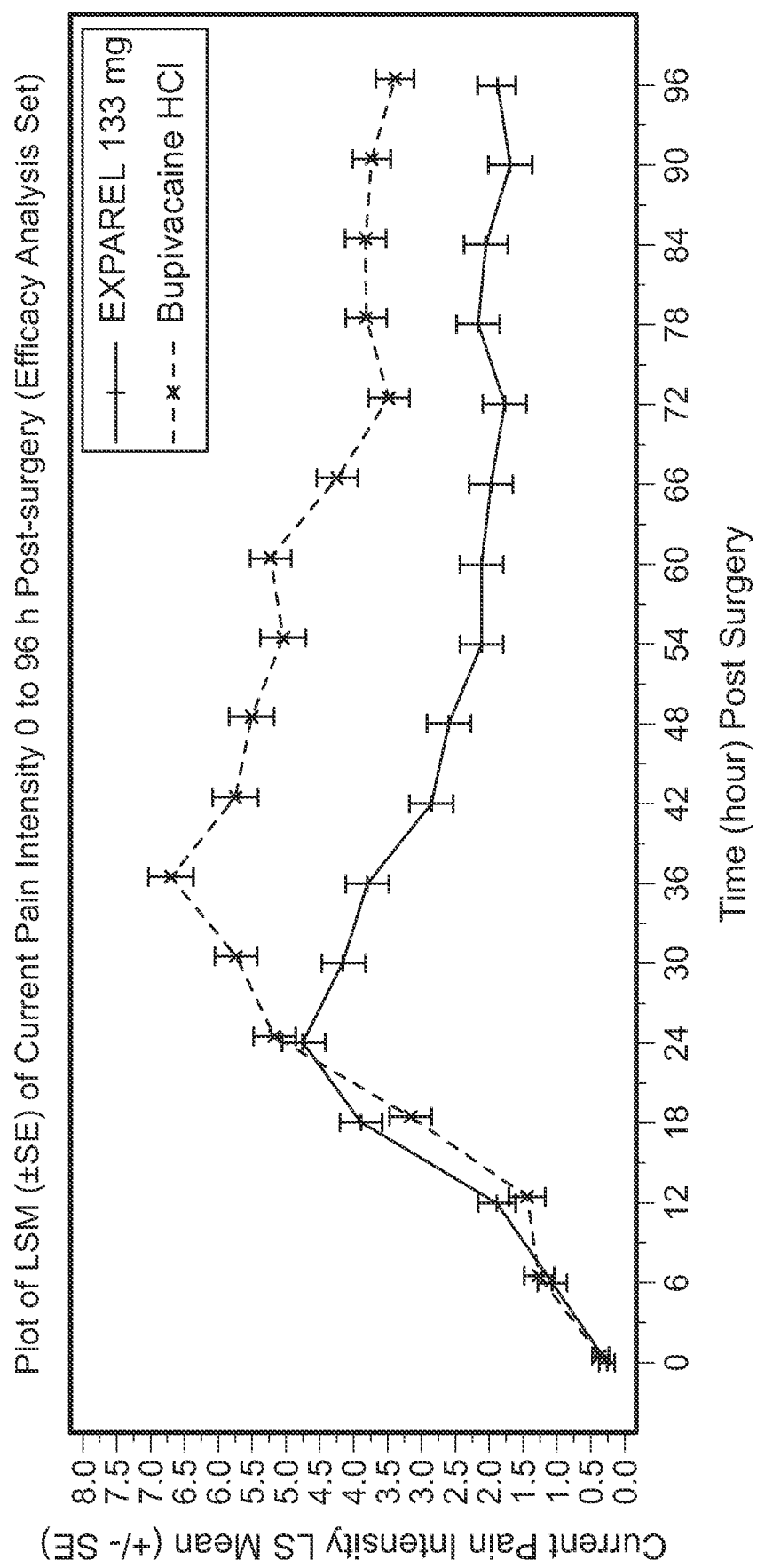
FIG. 13 shows a graph where from 30 to 96 h post-surgery (Part A+B), the EXP133 arm had a significantly lower mean current pain intensity than the BUP50 arm (p-values ≤0.00008).

Unless otherwise defined, all technical and scientific terms used herein have the same meaning as commonly understood by one of ordinary skill in the art to which this disclosure belongs. Although methods and materials similar to those described herein can be used in the practice or testing of the present disclosure, suitable methods and materials are described below. All publications, patent applications, patents, and other references mentioned herein are incorporated by reference in their entirety. In addition, the materials, methods, and examples are illustrative only and not intended to be limiting.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "pain" means a physiologic and/or psychologic reaction or response to potential or actual stimulus that may result in tissue damage, injury, disease, or other condition(s). Types of pain include but are not limited to acute pain, chronic pain, thermal pain, traumatic pain, chemical pain, inflammatory pain, ischemic pain, blunt pain, sharp pain, prickling pain, visceral pain, and neuropathic pain.

Sciatic Nerve Block at the Popliteal Fossa

In some embodiments, the methods include administering a pharmaceutical composition to the sciatic nerve. In some embodiments, the pharmaceutical composition is administered to the sciatic nerve at the level of the popliteal fossa. In some embodiments, the method includes administering a pharmaceutical composition to a peroneal and/or a tibial nerve. In some embodiments, the method includes administering a pharmaceutical composition to a peroneal and a tibial nerve. The sciatic nerve can be described a long and thick nerve made up of five nerve roots, two from the lower back region called the lumbar spine and three from the final section of the spine called the sacrum. The five nerve roots come together to form a right and left sciatic nerve. One sciatic nerve runs through each side of the body, through the hips, buttocks and down a leg, ending just below the knee. There, the sciatic nerve branches into other nerves, which continue down the leg and into the foot and toes. The sciatic nerve bifurcates into the tibial (medial) and common peroneal (lateral) nerves at approximately 6 to 10 cm proximal to the popliteal crease, though there is significant anatomic variation in the location of the split. A common sheath envelops these two nerves from their origin in the pelvis, which is distinctly separate from the epineurium of each nerve. Ultrasound imaging has shown that injecting local anesthetic within this sheath consistently gives a rapid onset, safe, and effective block. As the sciatic nerve descends toward the knee, the two components eventually diverge just proximal to the popliteal fossa, giving rise to the tibial and common peroneal nerves. The nerves traverse the diamond-shaped popliteal fossa, which is bounded laterally by the biceps femoris tendon and medially by the semitendinosus and semimembranosus tendons. The division of the sciatic nerve usually occurs between 50 and 120 mm proximal to the popliteal fossa crease. Following its divergence from the sciatic nerve, the peroneal nerve continues its path laterally and descends along the head and neck of the fibula. Its major branches in this region are branches to the knee joint and cutaneous branches that form the sural nerve. Its terminal branches are the superficial and deep peroneal nerves. The tibial nerve is the larger of the two divisions of the sciatic nerve and continues its path vertically through the popliteal fossa. Its terminal branches are the medial and lateral plantar nerves. Its collateral branches give rise to the cutaneous sural nerves, muscular branches to the muscles to the calf, and articular branches to the ankle joint.

In some embodiments, administering a pharmaceutical composition to the sciatic nerve includes a sciatic nerve block. In some embodiments, administering a pharmaceutical composition to the sciatic nerve, at the level of the popliteal fossa, includes a popliteal block. In some embodiments, administering a pharmaceutical composition to the sciatic nerve is an injection into the sheath of the sciatic nerve. In some embodiments, a sciatic nerve block can be used to deliver sensory anesthesia for procedures involving the lower leg and/or foot (e.g., calf, tibia, fibula, ankle, and foot). In some embodiments, a sciatic nerve block can be used to deliver sensory anesthesia for distal branches of the peroneal and/or tibial nerves. In some embodiments, administering a pharmaceutical composition to the sciatic nerve can be the administration of a sensory nerve block and/or a motor nerve block. In some embodiments, the sciatic nerve can be accessed through the lateral thigh.

In some embodiments, the sciatic nerve and/or popliteal fossa can be located in the patient leg by way of surface landmarks. In some embodiments, the sciatic nerve and/or popliteal fossa can be located by way of ultrasound guidance. In some embodiments, the sciatic nerve and/or popliteal fossa can be located a combination of surface landmarks and ultrasound guidance.

Pharmaceutical Compositions

Provided herein are analgesic pharmaceutical compositions. In some embodiments the pharmaceutical compositions are useful for the amelioration of post-operative analgesic pain.

In some embodiments, the pharmaceutical compositions include multivesicular liposomes. Multivesicular liposomes (or "MVL", which is used herein to refer to a multivesicular liposome or a plurality of multivesicular liposomes) are lipid vesicles having multiple non-concentric internal aqueous chambers having internal membranes distributed as a network throughout the MVL. The chambers may contain acids which are effective to enable the encapsulation of bupivacaine or a salt thereof and to modulate its release rate. A preparation of MVL is described, for example, in Kim et al., Biochim. Biophys. Acta 728, 339-348, 1983. In some embodiments, a MVL is prepared in accordance with a process as described in U.S. Pat. No. 9,192,575, incorporated by reference herein in its entirety. In some embodiments, a MVL is prepared in accordance with a process as described in U.S. Pat. No. 8,182,835, incorporated by reference herein in its entirety. In some embodiments, a MVL is prepared in accordance with a process as described in U.S. Pat. No. 8,834,921, incorporated by reference herein in its entirety. In some embodiments, a MVL is prepared in accordance with a process as described in U.S. Pat. No. 9,205,052, incorporated by reference herein in its entirety.

In some embodiments the multivesicular liposomes ("MVL") are made by the following process. A "water-in-oil" type emulsion containing a non-hydrohalic acid salt of bupivacaine, such as bupivacaine phosphate, is formed from two immiscible phases, a lipid phase and a first aqueous phase. The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamines.

Suitable neutral lipids are triglycerides, propylene glycol esters, ethylene glycol esters, and squalene. Examples of triglycerides useful in the present disclosure are triolein, tripalmitolein, trimyristolein, trilinolein, tributyrin, tricaproin, tricaprylin, and tricaprin. The fatty chains in the triglycerides useful in the present disclosure can be all the same, or not all the same (mixed chain triglycerides), including all different. Both saturated and unsaturated fatty chains are useful in the present disclosure. The propylene glycol esters can be mixed diesters of caprylic and capric acids.

Many types of volatile organic solvents can be used in the present disclosure, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the compositions of the present disclosure.

Optionally, other components are included in the lipid phase. Among these are cholesterol or plant sterols.

The first aqueous phase includes bupivacaine or a salt thereof, such as bupivacaine phosphate, at least one polyhydroxy carboxylic acid, and at least one di- or tri-protic mineral acid. In some embodiments, also included is hydrochloric acid. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about mM, or preferably from about 0.5 mM to about 25 mM.

The lipid phase and first aqueous phase are mixed by mechanical turbulence, such as through use of rotating or vibrating blades, shaking, extrusion through baffled structures or porous pipes, by ultrasound, or by nozzle atomization, to produce a water-in-oil emulsion. Thus, bupivacaine or a salt thereof, such as bupivacaine phosphate, is encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the bupivacaine or a salt thereof, such as bupivacaine phosphate, dissolved therein. The second aqueous phase can contain additional components such as glucose, and/or lysine.

The volatile organic solvent is then removed from the spherules, for instance by surface evaporation from the suspension: When the solvent is substantially or completely evaporated, MVL are formed. Gases which can be used for the evaporation include nitrogen, argon, helium, oxygen, hydrogen, and carbon dioxide. Alternatively, the volatile solvent can be removed by sparging, rotary evaporation, or with the use of solvent selective membranes.

In some embodiments, an MVL is prepared in accordance with a process as described in U.S. Pat. No. 10,398,648, incorporated by reference herein in its entirety. In some embodiments, a MVL is prepared in accordance with a process as described in U.S. Pat. No. 9,585,838 incorporated by reference herein in its entirety.

In some embodiments, an MVL is prepared in accordance with a process as described in US Published Patent Applications US 2011-0250264, US 2013-0306759, US 2013-0177634, US 2013-0177633, US 2013-0177635, US 2013-0195965, US 2013-0177636, US 2013-0183373, US 2013-0177638, US 2013-0177637, US 2013-0183372, US 2013-0183375, US 2016-0361260 or US 2018-0092847, each of which is incorporated by reference herein in its entirety.

In some embodiments, an MVL is prepared in accordance with a process as described in U.S. Pat. Nos. 11,033,495; 11,179,336; 11,278,494; 11,304,904; 11,311,486; 11,357,727; 11,426,348; 11,452,691, each of which is incorporated by reference herein in its entirety.

In some embodiments, the pharmaceutical compositions described herein can be combined, used in conjunction with, or used in an anesthetic or analgesic program with other anesthetics or analgesics.

Examples of anesthetics, include but are not limited to, propofol, etomidate, methohexital and sodium thiopental, midazolam, diazepam, and ketamine, benzocaine, chloroprocaine, cocaine, cyclomethycaine, dimethocaine, propoxycaine, procaine, proparacaine, tetracaine, articaine, bupivacaine, carticaine, dibucaine, etidocaine, levobupivacaine, lidocaine, mepivacaine, piperocaine, prilocaine, ropivacaine, trimecaine, saxitoxin, and tetrodotoxin. Examples of amide anesthetics, include but are not limited to, articaine, bupivacaine, carticaine, dibucaine, etidocaine, levobupivacaine, lidocaine, mepivacaine, piperocaine, prilocaine, ropivacaine, and trimecaine. In some embodiments, the multivesicular liposomes further comprise bupivacaine, morphine, cytarabine, or their pharmaceutically acceptable salts as the therapeutic agent. In some embodiments, the multivesicular liposomes further comprise bupivacaine phosphate, morphine sulfate, or cytarabine HCl.

The term "therapeutically effective" as it pertains to bupivacaine or a salt thereof, such as bupivacaine phosphate, present in the pharmaceutical compositions described herein, means that an anesthetic present in the first aqueous phase within the multivesicular liposome is released in a manner sufficient to achieve a particular level of anesthesia. Exact dosages will vary depending on such factors as the particular anesthetic, as well as patient factors such as age, sex, general condition, patient size, and the like. Those of skill in the art can readily take these factors into account and use them to establish effective therapeutic concentrations without resort to undue experimentation.

As used herein, "non-liposomal bupivacaine" refers to bupivacaine or a salt thereof that is not in liposomal form. For example, "non-liposomal bupivacaine" refers to bupivacaine or a salt thereof that is not comprised in a multivesicular liposome. The term "non-liposomal bupivacaine" encompasses compositions comprising bupivacaine, or a salt thereof, that is not in liposomal form.

Examples of analgesics can include opioid analgesics and non-opioid analgesics. Non-limiting examples of opioid analgesics include hydrocodone, oxycodone, propoxyphene, or fentanyl, thiosemicarbazone, p-nitrophenylhydrazone, o-methyloxime, semicarbazone, or bis (methylcarbamate), oxycodone, a pharmaceutically acceptable salt or its thiosemicarbazone, p-nitrophenylhydrazone, o-methyloxime, semicarbazone, or bis-methylcarbamate. Non-limiting examples of non-opioid analgesics useful in the present invention include aspirin; acetaminophen; a non-steroidal anti-inflammatory drug (NSAID), an arylalkanoic acid, a profen, a fenamic acid, an oxicam, a pyrazolidine derivative; a Cox-2 inhibitor, a local analgesic, an anti-depressant, an atypical analgesic, a psychotropic agent, an NMDA receptor antagonist, an α2-adrenoreceptor agonists and a synthetic drug having narcotic properties.

Embodiments of the present disclosure also include compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Academic Press, (Adeboye Adejareedit edit, 2020), hereby incorporated by reference in its entirety.

A pharmaceutically effective dose is that dose required to prevent, inhibit the occurrence, or treat (alleviate a symptom to some extent, preferably all of the symptoms) pain. One skilled in the art appreciates that compositions and methods of the present disclosure can be used to treat multiple types of pain, and that the effective dose may be different for different types of pain. Types of pain include but are not limited to thermal pain, chemical pain, inflammatory pain, ischemic pain, traumatic pain, blunt pain, sharp pain, prickling pain, and visceral pain. The pharmaceutically effective dose depends on the type of condition (e.g., pain), the composition used, the route of administration, the type of mammal being treated, the physical characteristics of the specific mammal under consideration (including but not limited to age, physical condition, surgical or other medical procedures being performed, circulatory capacity, cardiovascular function, pain tolerance, nerve function, liver function), concurrent medication, and other factors that those skilled in the medical arts will recognize.

Methods of Administering

Provided herein are methods of administering to a peroneal and a tibial nerve of a patient a pharmaceutical composition for post-operative analgesia, comprising: (a)

selecting an entry point of an injection needle in a leg of a patient; (b) inserting the injection needle into the patient at the entry point; (c) administering to a sciatic nerve of the patient via the injection needle saline and a pharmaceutical composition; wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the peroneal and the tibial nerve of the patient the pharmaceutical composition for post-operative analgesia.

Provided herein are methods of administering to a peroneal and a tibial nerve of a human patient a pharmaceutical composition for post-operative analgesia, comprising: (a) selecting an entry point of an injection needle in a leg in a patient; (b) advancing a needle tip of the injection needle within a region where the sciatic nerve splits into the peroneal and tibial nerves of the patient along a trajectory that extends between the entry point and where the sciatic nerve splits into the peroneal and tibial nerves; (c) administering to said region through the injection needle saline and a therapeutically effective amount of a pharmaceutical composition; wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the peroneal and the tibial nerve of the human patient the pharmaceutical composition for post-operative analgesia.

Provided herein are methods of treating post-operative foot pain in a patient, comprising: (a) selecting an entry point of an injection needle in a leg of the patient; (b) inserting the injection needle into the leg of the patient at the entry point; (c) administering to the patient saline and a pharmaceutical composition within a sciatic nerve sheath; wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby treating post-operative foot pain in the patient.

Provided herein are methods of administering a peroneal and a tibial nerve block to a patient to reduce post-operative foot pain, comprising: (a) selecting an entry point of an injection needle in a leg of a patient, wherein the entry point comprises the lateral thigh; (b) advancing a needle tip of the injection needle within a region where the sciatic nerve splits into the peroneal and tibial nerves of the patient along a trajectory that extends between the entry point and the region where the sciatic nerve splits into the peroneal and tibial nerves; (c) piercing with the needle tip of the injection needle the sciatic nerve sheath in said region; (d) administering through the injection needle saline and a therapeutically effective amount of a multivesicular liposome pharmaceutical composition; wherein the multivesicular liposome pharmaceutical composition comprises: bupivacaine or a salt thereof; phosphoric acid; a lipid component comprising at least one amphipathic lipid and at least one neutral lipid lacking a hydrophilic head group; and, optionally, a cholesterol and/or a plant sterol, thereby administering a peroneal and the tibial nerve block to the patient.

In some embodiments, the pharmaceutical composition is administered around or within a volume of 30 ml.

In some embodiments, the efficacy of a lower dose of MVL exceeds the efficacy of a higher dose of MVL. In some embodiments, a lower dose of MVL is between 100 and 150 mg MVL. In some embodiments, a higher dose of MVL is between 250 and 300 mg. In some embodiments, efficacy is defined as understood in the art. In some embodiments, efficacy is an improvement in any of the outcomes monitored in the studies described herein. Having a lower dose of MVL be more efficacious than a higher dose of MVL was surprising because it was expected that higher doses of MVL would produce a greater effect.

In some embodiments, the methods of the disclosure produce unexpectedly good anesthesia such that fewer rescue pain medications are needed to manage post-operative pain. In some embodiments, the methods of the disclosure produce unexpectedly good anesthesia such that a multimodal analgesic regimen (a non-opioid analgesic followed by an opioid analgesic) is not needed for post-operative pain rescue. In some embodiments, the methods of the disclosure produce unexpectedly good anesthesia such that much less or no opioids are needed for post-operative pain rescue. In some embodiments, the methods of the disclosure produce unexpectedly good anesthesia such that much less or no non-opioid medication is needed for post-operative pain rescue. In some embodiments, the methods of the disclosure produce unexpectedly good anesthesia such that only non-opioid medications are needed for post-operative pain rescue. In some embodiments, the methods of the disclosure produce unexpectedly good anesthesia such that only opioid medications are needed for post-operative pain rescue.

Routes of Administration

Anesthetics of the present disclosure may be delivered regionally or locally. "Regional" or "local" anesthesia, as used herein, is distinct from general anesthesia and refers to anesthetic procedures which allow for the preferential delivery of an anesthetic to a specific region of the body, such as near a nerve or a nerve bundle. In contrast, general anesthesia allows for the systemic administration of an anesthetic, e.g., via intravenous administration. Regional or local anesthesia typically allows for a lower total body concentration (although elevated local concentrations) of an anesthetic to be administered to a subject for analgesia or diminished pain perception of at least a portion of the subject's body. For example, intrathecal anesthesia, epidural anesthesia, and nerve blocks are examples of regional or local anesthesia.

A pharmacological composition can refer to a composition in a form suitable for administration, e.g., perineural administration, into a subject or proximal to at least one nerve of a subject, including for example wherein the subject is a human. Suitable forms, in part, depend upon the use or the route of entry. Examples of routes of entry include but are not limited to injection (including but not limited to subcutaneous injection), single injection, serial injection, indwelling catheter, and continuous infusion. Such routes of entry should not prevent the composition from reaching a target cell (i.e., a neuron). For example, injectable pharmacological compositions should be soluble. Other factors are known in the art, and include considerations such as toxicity and forms that prevent the composition or formulation from exerting its effect.

EXAMPLES

Example 1—Clinical Trial #1

A multicenter, randomized, double-blind clinical trial examining efficacy and safety of the pharmaceutical composition comprising: a) the multivesicular liposome disclosed herein and b) the aqueous phase disclosed herein, wherein the aqueous phase is encapsulated within the multivesicular liposome, was performed as described below. The pharmaceutical composition is referred to below as the "multivesicular liposomal" pharmaceutical composition, or "MVL".

The trial compared the magnitude of the postsurgical analgesic effect following a single dose of the MVL admixed with bupivacaine HCl vs. bupivacaine HCl when administered via an sciatic nerve block in subjects undergoing bunionectomy. Further, the trial compared post-surgical opioid consumption following a single dose of EXPAREL vs. bupivacaine HCl. Additionally, the trial compared the time to first opioid consumption post-surgery, following a single dose of EXPAREL vs. bupivacaine HCl. Further, the trial assessed the safety profile of EXPAREL and bupivacaine HCl.

| Abbreviation | Definition |
| --- | --- |
| $\lambda_z$ | Apparent terminal elimination rate constant |
| AE | Adverse event |
| AESI | Adverse event of special interest |
| ANCOVA | Analysis of covariance |
| ASA | American Society of Anesthesiologists |
| AUC | Area under the curve |
| $AUC_{0-\infty}$ | Area under the curve from the time of dosing to infinity |
| $AUC_{0-last}$ | Area under the curve from the time of dosing to the of the last quantifiable concentration |
| BLOQ | Below the limit of quantification |
| BMI | Body mass index |
| CFR | Code of Federal Regulations |
| CI | Confidence interval |
| CL/F | Apparent clearance |
| $C_{max}$ | Maximum plasma concentration |
| CMH | Cochran-Mantel-Haenszel |
| COVID-19 | Coronavirus disease 2019 |
| CV | Coefficient of variation |
| Diff | Difference |
| eCRF | Electronic case report form |
| EKG | Electrocardiogram |
| FDA | Food and Drug Administration |
| GCP | Good Clinical Practice |
| h | Hour(s) |
| $H_a$ | Alternative hypothesis |
| HCF | Health care facility |
| HCl | Hydrochloride |
| ICF | Informed consent form |
| ICH | International Council for Harmonisation |
| ID | Identification |
| IEC | Independent Ethics Committee |
| Intra-op | Intra-operative |
| IPO | International Pain Outcome |
| IRB | Institutional Review Board |
| IV | Intravenous(ly) |
| KM | Kaplan-Meier |
| LLOQ | Lower limit of quantification |
| LOCF | Last observation carried forward |
| LS(M) | Least squares (mean) |
| Max | Maximum |
| MedDRA | Medical Dictionary for Regulatory Activities |
| Min | Minimum |
| min | Minute(s) |
| NC | Not computed |
| NCA | Noncompartmental analysis |
| NRS | Numeric rating scale |
| NS | Normal saline |
| NSAID | Non-steroidal anti-inflammatory drug |
| OMED | Oral morphine equivalent |
| OR | Operating Room |
| PACU | Post-anesthesia Care Unit |
| PD | Pharmacodynamic(s) |
| PK | Pharmacokinetic(s) |
| PO | Orally administered |
| POD | Post-operative day |
| Post-op | Post-operative |
| PP | Predictive power |
| Pre-op | Pre-operative |

-continued

| Abbreviation | Definition |
| --- | --- |
| PRN | As needed |
| PT | Preferred term |
| Reduct | Reduction |
| SAE | Serious adverse event |
| SAP | Statistical analysis plan |
| SD | Standard deviation |
| SE | Standard error |
| SOC | System organ class |
| $t_{1/2el}$ | Apparent terminal elimination half-life |
| TEAE | Treatment-emergent adverse event |
| $T_{max}$ | Time to maximum plasma concentration |
| $V_d/F$ | Apparent volume of distribution |
| WOCBP | Women of child-bearing potential |

Inclusion Criteria

Each subject had to meet the following criteria to be eligible for the study:
1. Male or female, ages 18 or older at Screening.
2. American Society of Anesthesiologists (ASA) physical status 1, 2, or 3.
3. Able to provide informed consent, adhere to the study schedule, and complete all study assessments
4. Primary surgical indication was related to a bunion deformity (i.e., hallux valgus) and subject was scheduled to undergo a distal metaphyseal osteotomy procedure (e.g., Austin procedure as opposed to Lapiplasty, Lapidus bunionectomies or base wedge bunionectomies).
5. Indicated to undergo elective (i.e., not emergency) bunionectomy.
6. Body mass index (BMI)≥18 and <40 kg/m2.

Exclusion Criteria

Subjects who met any of the following criteria were excluded from the study:
1. Allergy, hypersensitivity, intolerance, or contraindication to any of the study medications for which an alternative was not named in the Protocol (e.g., amide-type local anesthetics, opioids, bupivacaine HCl, and non steroidal anti-inflammatory drugs [NSAIDs]).
2. Concurrent painful physical condition (e.g., arthritis, fibromyalgia, and cancer) that may have required analgesic treatment with NSAIDs or opioids in the post-dosing period for pain that was not strictly related to the foot surgery and which may have confounded the post-dosing assessments.
3. Inadequate sensory function of the foot/ankle as assessed.
4. History of, suspected, or known addiction to or abuse of illicit drug(s), prescription medicine(s), or alcohol within the past 2 years.
5. Administration of an investigational drug within 30 days or 5 elimination half-lives of such investigational drug, whichever was longer, prior to study drug administration, or planned administration of another investigational product or procedure during the subject's participation in this study.
6. Previous participation in an EXPAREL study.
7. Uncontrolled anxiety, schizophrenia, or other psychiatric disorder that could interfere with study assessments or compliance.
8. Currently pregnant, nursing, or planning to become pregnant during the study.
9. Clinically significant medical disease that would have made participation in a clinical study inappropriate. This included diabetic neuropathy, coagulation, or bleeding disorders, severe peripheral vascular disease, renal insufficiency, hepatic dysfunction, or other conditions that would have constituted a contraindication to participation in the study.
10. Currently on a neuromodulating agent (e.g., gabapentin, pregabalin [Lyrica®], duloxetine [Cymbalta®], etc.).
11. Current use of systemic glucocorticoids within 30 days of randomization in this study.
12. Use of dexmedetomidine HCl (Precedex®) or clonidine within 3 days of study drug administration.
13. Any use of marijuana (including tetrahydrocannabinol and cannabidiol) within 30 days prior to randomization, or planned use during the course of the study.
14. Chronic opioid use within 30 days prior to randomization (average ≥30 OMED/day).

Methods

Clinical Study #1 was a Phase 3, multicenter, randomized, double-blind, active-controlled study in 180 subjects undergoing bunionectomy. Subjects received a sciatic (in the popliteal fossa) nerve block with a single dose of either EXPAREL 266 mg (EXP266), EXPAREL 133 mg (EXP133), or 0.25% bupivacaine HCl (50 mg; BUP50). The study was conducted in two parts (Part A and Part B). Part A was to be completed and analyzed before enrollment in Part B was initiated. Part A was a 3-arm cohort with 66 subjects undergoing bunionectomy to obtain information on pharmacokinetics (PK), pharmacodynamics (PD), efficacy, and safety. Subjects were randomized (1:1:1) to the EXP266, EXP133, and BUP50 treatment arms. Part B was a 2-arm cohort with 119 subjects undergoing bunionectomy to evaluate the efficacy and safety of EXPAREL compared with bupivacaine HCl. The dose of the EXPAREL arm in Part B was determined based on the interim analysis of the Part A cohort results.

Subject participation began upon obtaining informed consent, which was obtained within days prior to administration of the study drug. Screening procedures included assessment of eligibility; recording of medical/surgical history, prior and concomitant medications (related to medical history), demographics and baseline characteristics, and height and weight for body mass index (BMI) calculation; assessment of chronic opioid and any cannabis use in the past days (average ≥30 OMED/day); urine pregnancy test for women of childbearing potential (WOCBP); 12-lead electrocardiogram (EKG); and monitoring of adverse events (AEs) and serious adverse events (SAEs).

On the day of surgery, subjects received an ultrasound-guided sciatic (in the popliteal fossa) nerve block with one of the following treatments:
EXP266 arm: subjects randomized to this treatment arm received 20 mL (266 mg) EXPAREL mixed with 10 mL saline (Part A only; per interim analysis was not selected for Part B)
EXP133 arm: subjects randomized to this treatment arm received 10 mL (133 mg) EXPAREL mixed with 20 mL saline (Part A and B)
BUP50 arm: subjects randomized to this treatment arm received 20 mL (50 mg) 0.25% bupivacaine HCl mixed with 10 mL saline (Part A and B)

All subjects in Part A and Part B received a Mayo field block with 20 mL of 0.5% bupivacaine HCl after study drug administration.

Treatment prior to study drug administration could have included Celecoxib 200 mg orally administered within 4 hours prior to surgery. Other permitted prior medications and therapy include 1 to 2 mg of midazolam and/or ondansetron. Restricted medications and therapy prior to drug study administration included systemic glucocorticosteroids and neuromodulating agents (e.g., gabapentin, pregabalin [Lyrica®], duloxetine [Cymbalta®], etc.); no long-acting or sustained release opioid medications and NSAIDs (except for low-dose acetylsalicylic acid used for cardiovascular protection) within 3 days of study drug administration; no dexmedetomidine HCl (Precedex®) or clonidine within 3 days of study drug administration; no scopolamine patches; no opioid medications within 24 hours of study drug administration; no use of an investigational product within 30 days or 5 elimination half-lives of such investigational drug, whichever was longer, prior to study drug administration, or planned administration of another investigational product or procedure during the subject's participation in this study was not permitted; no drugs (other than the described bupivacaine HCl admixture) were to be admixed with study drug (e.g., epinephrine, dexamethasone, clonidine); no lidocaine or other local anesthetics were locally administered in the area of the nerve block administration other than use in a superficial cutaneous wheal for needle insertion.

Perioperative treatment. Perioperative treatment included receiving a Mayo field block with 20 mL 0.5% bupivacaine HCl immediately following study drug administration (was to be done with the same set-up for the nerve block). A participant could have received 1000 mg of IV acetaminophen at the time of surgical incision, single-dose administration of ondansetron or metoclopramide for nausea, or propofol for induction and intra-operative sedation. Restricted medications included no other medication (including opioids) were to be mixed with the bupivacaine for spinal anesthesia; no use of dexamethasone, acetaminophen, ketorolac, or other NSAIDs preemptively or intra operatively, except for emergency use to treat an AE; no intra operative use of opioids (except IV fentanyl at a dose not exceeding 1 µg/kg, unless deemed medically necessary) and ketamine. Neuraxial or regional anesthesias were not permitted. Lidocaine and other local anesthetics were not permitted to be locally administered in the area of the nerve block administration.

Postsurgical pain for breakthrough pain. An unscheduled pain intensity assessment using the NRS (measured as "On a scale from 0 to 10, where 0 equals no pain and 10 equals the worst possible pain, how much pain are you experiencing in your operative foot right now?") was to be completed immediately prior to administration of any breakthrough pain medication up to 96 h post-surgery. Medications were administered PRN; opioids were not to be given on a pre-determined schedule. Immediate release PO oxycodone could be administered in a stepwise approach as follows: initial doe of 5 mg oxycodone offered; if the initial opioid dose was insufficient for pain relief, an additional 5 mg oxycodone could be offered up to a maximum of 10 mg (total dose); if a subject was unable to tolerate PO medication or the PO oxycodone pain relief was insufficient, IV morphine (initiated at 2 mg) or hydromorphone (initiated at 0.2 mg) could be administered. No NSAIDs or other opioids, including tramadol were allowed for breakthrough pain management. No acetaminophen (other than the scheduled IV acetaminophen) was to be used for breakthrough pain. Pain management modalities were standardized during the first 96 h post-surgery. After 96 h, the analgesic regimen could be adjusted for each subject individually as deemed appropriate by the physician responsible for the postsurgical care. All postsurgical analgesics administered, were to be recorded through hospital discharge.

Efficacy assessments included pain intensity scores focused on the operative foot using the Numeric Rating Scale (NRS), total postsurgical opioid consumption in OMED, time to first opioid consumption post-surgery, and percentage of opioid-free patients through 96 hours, and worst and average NRS pain intensity scores at 24 h, 48 h, 72 h, and 96 h from end of surgery. Additionally, blood samples for pharmacokinetic (PK) analysis (area under the curve [AUC], maximum plasma concentration [Cmax], time of maximum plasma concentration [Tmax], including early and late Cmax and Tmax (EXP133-ADMIX arm only), apparent terminal elimination half-life [t1/2el], apparent clearance [CL/F], and apparent volume of distribution [Vd/F]). Pharmacodynamic (PD) assessment data, including median time to onset of sensory block and motor block, and median duration of sensory and motor block were collected.

Safety assessments included monitoring of AEs from the time of randomization through POD 14. Safety endpoints include incidence of treatment-emergent AEs and SAEs from the start of the nerve block procedure through POD 14.

End Points

The primary endpoint was the AUC of the NRS pain intensity scores from 0 to 96 hours post-surgery.

Secondary efficacy endpoints included total postsurgical opioid consumption in OMED from 0 to 96 hours post-surgery; percentage of opioid-free subjects through 96 hours; time to first opioid consumption post-surgery; and worst and average NRS pain intensity scores at 24, 48, 72, and 96 hours post-surgery.

Safety endpoints included incidence of treatment emergent adverse events (AEs) and serious adverse events (SAEs) from start of the nerve block procedure through POD14.

Pharmacokinetic endpoints included area under the plasma concentration-versus-time curve (AUC); maximum plasma concentration (Cmax) and time of maximum plasma concentration (Tmax); apparent terminal elimination half-life ($t_{1/2el}$); apparent clearance (CL/F); and apparent volume of distribution (Vd).

Pharmacodynamic endpoints included: onset of sensory block, offset of sensory block, duration of sensory block, onset of motor block, offset of motor block, and duration of motor block.

TABLE 1

Pharmacokinetic Parameters

| Parameter | Definition |
|---|---|
| $C_{max}$ | The maximum observed plasma concentration obtained directly from the concentration-time data |
| Early $C_{max}$[1] | The maximum observed plasma concentration occurring between dosing (0 h) and x h after dosing if appropriate based on the individual subject and treatment group mean concentration-time plots, where x was determined from the concentration-time plot |
| Late $C_{max}$[1] | The maximum observed plasma concentration occurring more than x h after dosing if appropriate based on the individual subject and treatment group mean concentration-time plots, where x was a subject-specific local minimum turning point in the concentration-time curve |
| $T_{max}$ | Time at which $C_{max}$ was observed |
| Early $T_{max}$[1] | Time at which early $C_{max}$ was observed |
| Late $T_{max}$[1] | Time at which late $C_{max}$ was observed |
| $\lambda_z$ | The apparent terminal elimination rate constant was estimated at the terminal phase by linear regression after log-transformation of the concentrations |
| $t_{1/2el}$ | The apparent terminal half-life was calculated as $\ln(2)/\lambda_z$ |
| $AUC_{0-last}$ | The area under the plasma concentration-time curve from the time of dosing to the time of the last quantifiable concentration; calculated using the linear-up/log-down trapezoidal method |
| $AUC_{0-\infty}$ | The area under the plasma concentration-time curve from the time of dosing (zero) to infinity; calculated as the sum of $AUC_{0-last}$ and residual area $C_t/\lambda_z$ |
| $AUC_{extr}$ | Extrapolated area under the curve from time of last point above LLOQ to infinity, expressed as percentage of $AUC_{0-\infty}$; calculated as $(C_t/\lambda_z)/AUC_{0-\infty} \times 100\%$. |
| CL/F | Apparent clearance was estimated as dose/$AUC_{0-\infty}$, where dose = 133 mg and 266 mg for subjects receiving EXPAREL 133 mg and 266 mg, respectively, and 44 mg (50 mg × 0.886 [salt to free base conversion]) for subjects receiving 50 mg bupivacaine HCl. |
| $V_d/F$ | Apparent volume of distribution was estimated as $(CL/F)/\lambda_z$ |

Abbreviations: HCL = hydrochloride; LLOQ = lower limit of quantitation; SAP = Statistical Analysis Plan.
[1]If a subject only received bupivacaine HCl, the plasma concentration-time curve was not expected to see an early and late phase separation.

Statistical Analysis

Descriptive statistics (number of subjects, mean, SD, median, minimum, and maximum) are provided for continuous data. Tabulations (number and percentage of subjects) by category are provided for categorical data. Safety analyses are summarized descriptively by treatment arms. The total sample size for Part A and B was calculated based on the primary outcome measure of NRS pain intensity scores. A sample size of 80 subjects per study arm [1:1 randomization, 80 EXPAREL (EXPAREL 266 or EXPAREL 133), 80 Bupivacaine HCl] provides at least 85% power to detect a treatment difference of 110 units in the AUCs (SD=230) comparing the EXPAREL arm with the Bupivacaine HCl arm at a one-sided 0.025 significance level. All tests will be either one-sided on a significance level of 0.025 or two-sided on a significance level of 0.05.

The AUC of NRS pain intensity scores from 0-96 hours post-surgery were analyzed using the analysis of covariance (ANCOVA) model.

Total postsurgical opioid consumption in oral morphine equivalents (OMED) from 0 to 96 hours is analyzed using the ANCOVA model. Time to first postsurgical opioid medication is analyzed using the Kaplan-Meier survival method. Worst and average NRS pain intensity scores through 24 h, 48 h, 72 h, and 96 h from the end of surgery are summarized by treatment arm.

Adverse event verbatim terms are mapped to preferred terms and related system organ class using the Medical Dictionary for Regulatory Activities (MedDRA). Events that start prior to the start of study drug administration are identified in a by-subject listings. Incidence rates of TEAEs and the proportion of subject prematurely withdrawn from the study due to a TEAE is shown for each treatment arm.

Incidence rates are also displayed for each treatment arm for TEAEs by severity and separately by relationship. Incidence rates of SAEs is shown for each treatment arm. All incidence rates are categorized and displayed by system organ class and preferred term.

Results

Efficacy

In Part A, there was a statistically significant difference in the LSM AUC of the NRS Pain Intensity Score from 0 to 96 h post-surgery between the EXP133 arm and BUP50 arm (LSM difference=−189.0; p=0.0012; FIG. 5); the difference was not significant between the EXP266 and BUP50 arm (p=0.1515; FIG. 5). In Part B, subjects in the EXP133 arm had a lower LSM AUC of NRS Pain Intensity Score from 0 to 96 h post-surgery compared with the BUP50 arm with an LSM difference of −160.2 (p<0.00001; FIG. 5). Similar results were observed when combining Part A and B subjects, with a corresponding 44.16% reduction in overall pain intensity for those in the EXP133 arm compared with the BUP50 arm (FIG. 6). After 24 h post-surgery, the EXP133 arm had significantly lower LSM AUC of NRS Pain Intensity Scores than the BUP50 arm overall (Part A+B) at all-time intervals (LSM difference range=−167.1 to −42.9; p values <0.00001; FIG. 6).

In Part A, the EXP133 arm had a geometric mean total opioid consumption approximately 2 fold lower than the EXP266 and BUP50 arms from 0 to 96 h post-surgery. Geometric mean total opioid consumption for EXP266 subjects in Part A was highest from 0 to 24 h post-surgery, decreasing over time at subsequent 24 h intervals, whereas EXP133 and BUP50 subjects had total opioid consumption peak at 24 to 48 h (Part A+B), before decreasing over time. Cumulatively, total opioid consumption was more than two-fold higher at 0 to 48 h (geometric mean range=4.44 to 11.29) compared with 0 to 24 h post-surgery (geometric mean range=10.06 to 24.60) in all treatment arms (FIG. 7). In Parts A+B combined, the EXP133 arm had a significantly lower total opioid consumption than the BUP50 arm with an LSM ratio of 0.39 from 0 to 96 h post-surgery (p<0.00001; FIG. 8). After 24 h post-surgery, the EXP133 arm had significantly lower total opioid consumption than the BUP50 arm at all-time intervals with LSM ratios over bupivacaine ranging from 0.23 to 0.44 (p values <0.00003; FIG. 8).

From 0 to 96 h post-surgery, estimates of the proportion of opioid-free subjects were 4.5% in the EXP266 arm (Part A), 33.3% in the EXP133 arm (Part A+B), and 9.8% in the BUP50 arm (Part A+B). Over the same time interval, subjects in the EXP133 arm were 5.04 times as likely to be opioid-free compared with the BUP50 arm (p=0.0003; FIG. 9).

Overall, the proportions of subjects who received opioid breakthrough medication were 95.5% in EXP266 (Part A), 67.9% in EXP133 (Part A+B), and 90.2% in BUP50 subjects (Part A+B). Median times to first rescue medication were 16.06 h in EXP266, 20.27 h in EXP133, and 20.68 h BUP50 subjects. In Parts A+B, the hazard ratio between EXP133 and BUP50 subjects was statistically significant at 0.65 (1 sided p value from Cox model=0.0089; FIG. 10).

Mean worst and average pain intensity scores were significantly lower in the EXP133 arm compared with the BUP50 arm on Days 2, 3, and 4 (LSM difference range=−3.3 to −2.1; p values <0.00001 and LSM difference range=−2.2 to −1.5; p-value <0.00001 for worst and average pain intensity, respectively; FIG. 12).

Estimate of opioid-free subjects were lower in EXP266 subjects (range=4.5 to 9.1%) compared with EXP133 (range=33.3 to 44.4%) and BUP50 (range=9.8 to 42.7%) subjects from Parts A and B at all-time intervals. Overall (Parts A+B), subjects in the EXP133 arm were 4.12 and 5.04 times as likely to be opioid free compared with the BUP50 arm at 0 to 48 h (p=0.0006) and 0 to 72 h post-surgery (p=0.0003), respectively (FIG. 9).

Subject satisfaction with pain management was similar amongst the 3 treatment groups with mean values between 9.0 and 9.3 out of 10.

Mean AUC of worst and average pain intensity in the EXP266 arm (Part A) was similar to the BUP50 arm (Part A+B), but both treatment arms were higher compared with the EXP133 arm (Part A+B). Mean AUC of worst pain over the last 24 h post-surgery from POD1 through POD4 was significantly different (LSM difference=9.1, p<0.00001) between the EXP133 and BUP50 arm with values of 16.1 and 25.2, respectively. Mean AUC of average pain over the last 24 h post-surgery from POD1 through POD4 was significantly different (LSM difference=−5.8, p<0.00001) between the EXP133 and BUP50 arm with values of 10.3 and 16.1, respectively.

Mean current pain intensity post-surgery peaked at 24 h post-surgery in the EXP133 arm, 30 h in the EXP266 arm, and 36 h in the BUP50 arm, gradually decreasing until 96 h post-surgery. From 30 to 96 h post-surgery (mean range=0.4 to 6.0 vs. mean range=0.1 to 4.2 in EXP133 [Part A+B] and 0.2 to 5.3 in BUP50 [Part A+B]), the EXP133 arm had a significantly lower mean current pain intensity than the BUP50 arm (p-values ≤0.00008; FIG. 13).

Exploratory Efficacy Measures

Estimates of opioid-free subjects were lower in EXP266 subjects (range=4.5 to 9.1%) compared with EXP133 (range=33.3 to 44.4%) and BUP50 (range=9.8 to 42.7%) subjects from Parts A and B at all-time intervals. Overall (Part A+B), subjects in the EXP133 arm were 4.12 and 5.04 times as likely to be opioid-free compared with the BUP50 arm at 0 to 48 h (p=0.0006) and 0 to 72 h post-surgery (p=0.0003), respectively. See FIG. 9.

Pharmacodynamics

Figure 16A:
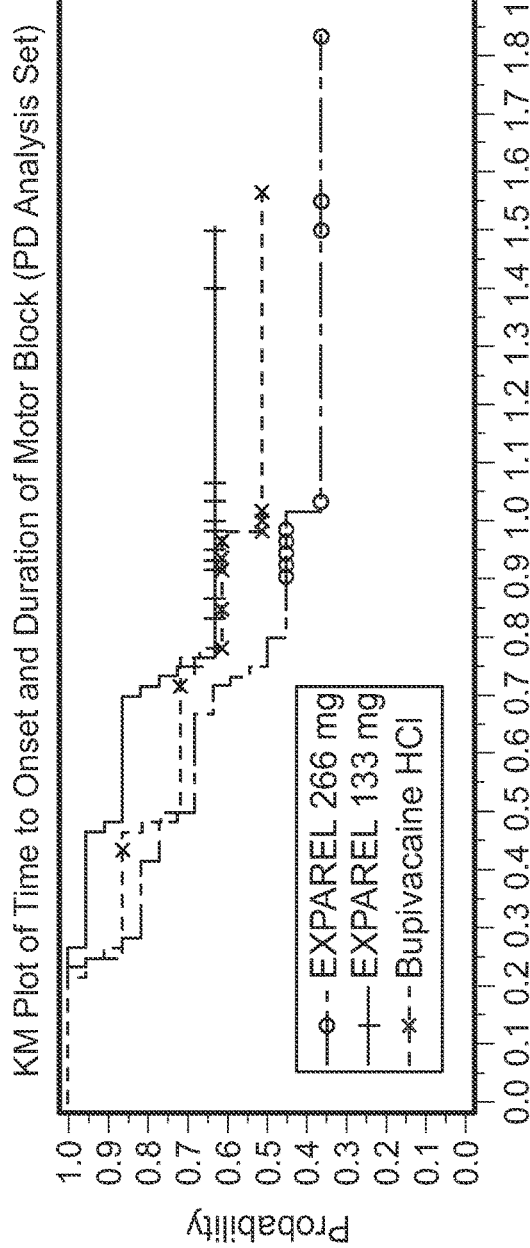
FIGS. 16A-B show FIG. 2, a KM plot of time to onset (FIG. 16A) and duration (FIG. 16B) of motor block for participants in clinical trial #1.
Figure 16B:
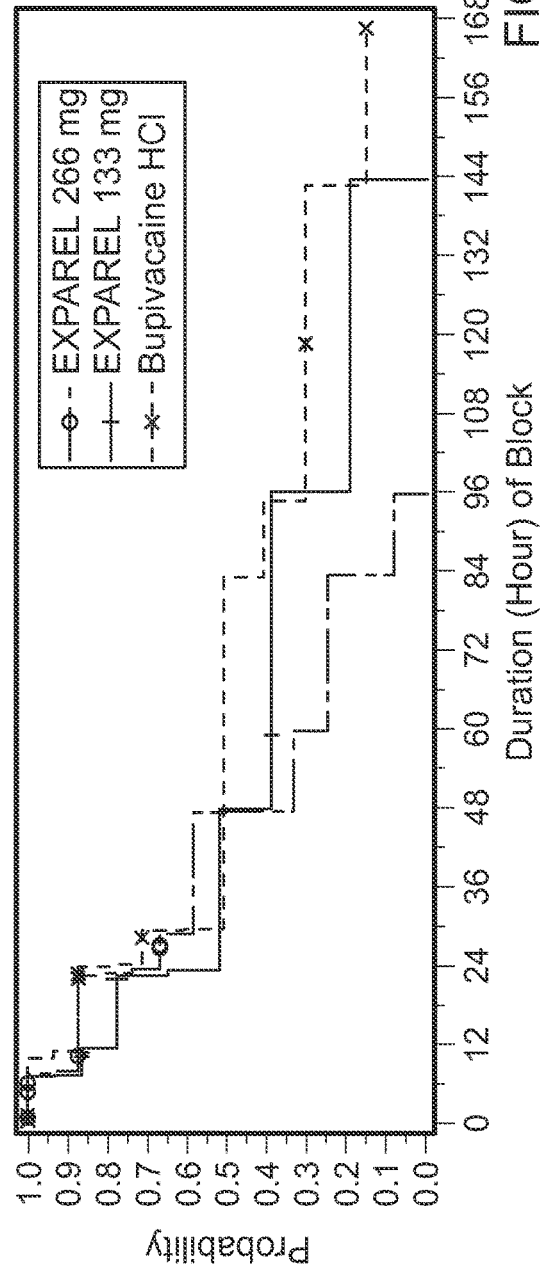

There were 59.1% of EXP266 subjects with motor block onset observed, compared with 36.4% and 40.9% of EXP133 and BUP50 subjects, respectively. The median time to motor block was not evaluable in all treatment arms. The difference between median duration of motor block was not statistically significant between treatment arms. The first time point at which foot movement was not present in ≥50% of subjects was 1 h post dose for the EXP266 arm (50.0%) and 2 h post-dose for the EXP133 and BUP50 arms (54.5% each). By 84 h post-dose, 18.2% of BUP50, 13.6% of EXP133, and 4.5% of EXP266 subjects still did not have complete foot movement (FIGS. 15 and 16).

Figure 17A:
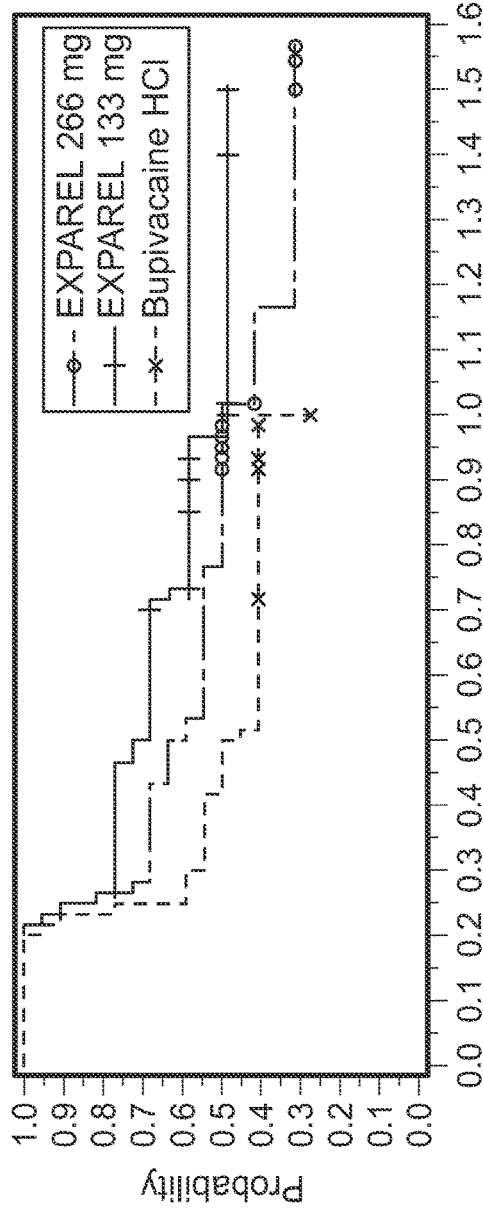
FIGS. 17A-B show FIG. 3, a KM plot of time to onset (FIG. 17A) and duration (FIG. 17B) of sensory nerve block for participants in clinical trial #1.
Figure 17B:
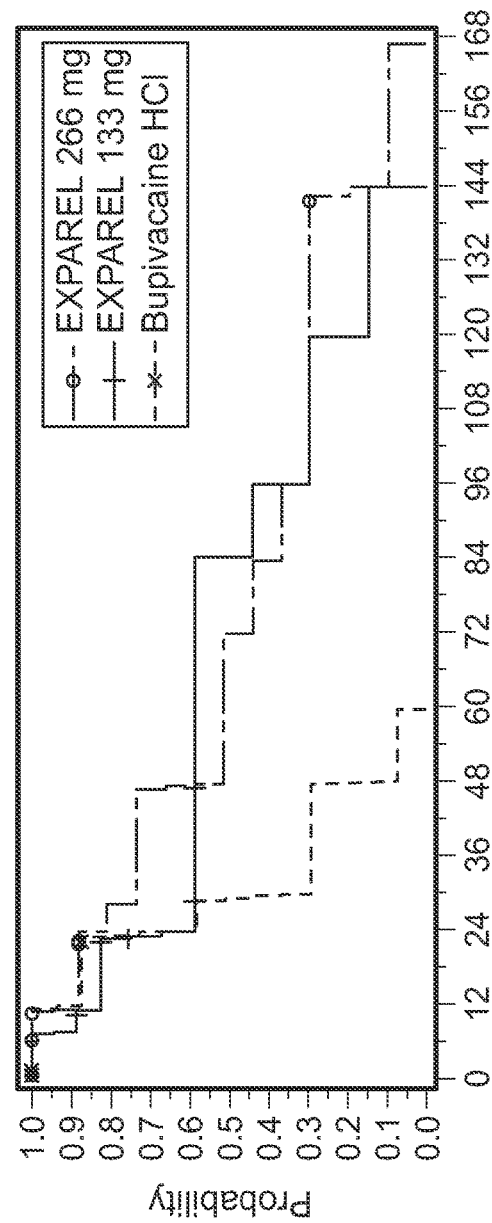

There were 59.1% of EXP266 and 63.6% of BUP50 subjects with sensory block onset observed, compared with 45.5% of EXP133 subjects. The median time to sensory block was 0.46 h in BUP50, 0.89 h in EXP266, and 0.97 h in EXP133 subjects. The median duration of sensory block was 2- to 3 fold longer in EXPAREL subjects (71.87 h in EXP266 and 84.28 h in EXP133) compared with BUP50 subjects (29.10 h); these differences were only statistically significant for EXP266 subjects (1-sided p-value from Cox model=0.0069). The first time point at which sensation was not present in ≥50% of subjects was 30 min post-dose for the BUP50 arm (59.1%) and 2 h for the EXP266 (68.2%) and EXP133 (59.1%) arms. At 60 h post-dose, 40.9% of EXP266 and 18.2% of EXP133 subjects still did not have completion sensation; conversely, all BUP50 subjects had regained sensation (FIGS. 15 and 17).

Safety

No deaths occurred during this study and EXPAREL was well tolerated by subjects.

A similar proportion of subjects across treatment groups reported TEAEs, which included 59.1% of EXP266 subjects, 54.9% of BUP50 subjects, and 51.9% of EXP133 subjects. The most common TEAEs were nausea (40.9%) and vomiting (22.7%) in EXP266 subjects, nausea (16.0%) and constipation (12.3%) in EXP133 subjects, and constipation (31.7%) and nausea (23.2%) in BUP50 subjects (FIG. 20).

A slightly higher proportion of subjects in the EXP266 arm had a treatment-related TEAE (Part A; 18.2%) compared with the EXP133 (Part A+B; 6.2%) and BUP50 (Part A+B; 2.4%) arms (FIG. 19). Hypertension and peroneal nerve palsy were the most common related events occurring in 3 and 2 subjects, respectively. Related TEAEs of moderate severity included hypertension, headache, vomiting, bradycardia, atrioventricular block second degree, and muscular weakness; all other events were of mild severity. The related event of arthralgia was assessed as probably related to study drug, while all other events were assessed as possibly related.

All TEAEs were of mild or moderate severity. Between 31.8% and 42.7% of subjects had a mild TEAE and 12.2% to 27.3% had a moderate TEAE across the treatment arms (FIG. 19). There was a higher proportion of subjects with moderate TEAEs in the EXP266 arm (27.3%) compared with 12.3% in the EXP133 arm and 12.2% in the BUP50 arm (FIG. 19). The most common moderate severity TEAEs were nausea, constipation, vomiting, and headache.

There were 3 subjects in the EXP133 arm and 4 subjects in the BUP50 arm who had ≥1 AESI, which included AESIs of muscle twitching, dizziness, peroneal nerve palsy, atrioventricular block second degree, and muscular weakness. Dizziness was the most common AESI, reported in 3 subjects. In the BUP50 arm, the AESIs of atrioventricular block second degree and muscular weakness were considered possibly related to study drug (1 subject each).

There was 1 subject in the EXP266 arm that had treatment-emergent SAEs of hypertension and pyrexia related to study drug and 1 subject in the BUP50 arm had an SAE of atrioventricular block second degree related to study drug; both subjects discontinued from the study due to SAEs. Two of the 3 SAEs (atrioventricular block second degree and hypertension) were of moderate severity and all SAEs resolved the same day as the start date. There were no other subjects with SAEs or TEAEs leading to study discontinuation.

Overall, there were minimal changes in mean vital sign values from baseline to post-surgery. Mean values also did not markedly differ across treatment arms. Mean systolic and diastolic blood pressure were generally lower following surgery across treatment arms.

From Screening to POD7, scheduled EKG assessments were normal or not clinically significant for most subjects, with 1 subject in the EXP133 and BUP50 arm having a clinically significant abnormal EKG finding on POD2 and POD1, respectively. Following study drug administration, clinically significant findings included 1 subject in the EXP133 arm with a sinus rhythm with poor R wave progression; 1 subject in the BUP50 arm had a clinically significant abnormality related to the SAE of second degree atrioventricular block.

Summary of Results and Conclusions

Efficacy Results—Pain Intensity Scores: EXP133 subjects had a significantly lower LSM AUC of NRS Pain Intensity Score than the BUP50 arm from 0 to 96 h post-surgery (LSM difference=−164.0; $p<0.00001$). After 24 h post-surgery, the EXP133 arm had significantly lower LSM AUC of NRS Pain Intensity Scores than the BUP50 arm at all-time intervals (LSM difference range=−167.1 to −42.9; p values <0.00001). Mean worst and average pain intensity scores were significantly lower in the EXP133 arm compared with the BUP50 arm on Days 2, 3, and 4 (LSM difference range=−3.3 to −2.1; p values <0.00001 and LSM difference range=−2.2 to 1.5; p value <0.00001 for worst and average pain intensity, respectively).

Efficacy Results—Postsurgical Opioid Consumption: The EXP133 arm had a significantly lower total opioid consumption than the BUP50 arm from 0 to 96 h post-surgery (LSM ratio=0.39; $p<0.00001$). Over the same time interval, subjects in the EXP133 arm were 5.04 times as likely to be opioid-free compared with the BUP50 arm (p=0.0003). The median time to first rescue medication was 20.27 h and 20.68 h in EXP133 and BUP50 subjects, respectively.

Pharmacodynamic Results: The difference between median duration of motor block was not statistically significant between treatment arms; conversely, the median duration of sensory block was 2 to 3-fold longer in EXPAREL subjects (71.87 h in EXP266 and 84.28 h in EXP133) compared with BUP50 subjects (29.10 h).

Safety Results: No deaths occurred during this study and EXPAREL was well tolerated by subjects. A similar proportion of subjects across treatment groups reported TEAEs, which included 59.1% of EXP266 subjects, 54.9% of BUP50 subjects, and 51.9% of EXP133 subjects. There were 3 subjects in the EXP133 arm and 4 subjects in the BUP50 arm who had ≥1 AESI. Dizziness was the most common AESI, reported in 3 subjects. Five subjects (6.2%) and 2 (2.4%) subjects had ≥1 TEAE related to study drug in the EXP133 and BUP50 arms, respectively. There was 1 subject who received EXPAREL (266 mg) and 1 subject who received bupivacaine HCl that had SAEs.

Adverse Events

An AE can be defined as any untoward medical occurrence associated with the use of a drug in humans, whether or not considered drug related. An AE (also referred to as an adverse experience) could be any unfavorable and unintended sign (e.g., abnormal laboratory finding), symptom, or disease temporally associated with the use of a drug, without any judgment about causality. An AE could arise from any use of the drug (e.g., off-label use in combination with another drug) and from any route of administration, formulation, or dose, including an overdose.

An AE could be any unfavorable and unintended change in a body structure or body function. Adverse events included any clinically significant deterioration of a subject's medical status. The AE could involve any organ or system and could be represented by the new onset or deterioration of a disease, syndrome, symptom, or physical sign, as well as by findings and results of instrumental examinations and laboratory tests. Any medically relevant and untoward change after the subject signed the ICF, including frequency or pattern changes for a fluctuating condition (e.g., migraine), was considered an AE.

An AE that occurred after administration of the study treatment was considered a treatment-emergent adverse event (TEAE). A continuous AE with varying grades of severity was to be recorded as 1 AE. The highest grade of severity experienced by that subject during the course of the continuous AE was to be recorded.

In general, the severity of an AE was to be categorized using the following guidelines:
  Mild: An AE that was easily tolerated by the subject, caused minimal discomfort, and did not interfere with everyday activities.
  Moderate: An AE that was discomforting and interfered with normal everyday activities.
  Severe: An AE that prevented normal everyday activities.
  Assessment of the relationship of the AE to study drug after careful medical consideration on a case-by-case basis. General guidelines are provided below:
  Unrelated: A causal relationship between the study drug and the AE could be easily ruled out (e.g., based on the temporal sequence, absence of a reasonable pathophysiological mechanism, or direct evidence of actual cause).
  Unlikely: A clinical event with a temporal relationship to study drug administration that made a causal relationship improbable and in which other drugs, chemicals, or underlying disease provided a plausible explanation.
  Possible: A clinical event with a reasonable time sequence to administration of the study drug but that could also be explained by a concurrent disease or other drugs or chemicals.
  Probable: A clinical event with a reasonable time sequence to administration of the study drug unlikely to be attributed to a concurrent disease or other drugs or chemicals and that followed a clinically reasonable response on withdrawal (dechallenge).
  Definite: The pharmacological properties of the study drug(s) or of the substance class, and the course of the AE after dechallenge and, if applicable, after rechallenge, and/or specific test indicated involvement of the study drug(s) in the occurrence/worsening of the AE, and no indication of other causes existed.

Based on review of all peripheral nerve blocks, the following conditions were considered to be Adverse Events of Special Interest (AESIs) upon review of the AEs:
  Falls
  Persistent tingling
  Persistent numbness
  Persistent weakness
  Hypersensitivity
  Seizures
  Tremors
  Dizziness
  Hematoma formation
  Cardiovascular depression
  Dyspnea
  Cardiovascular arrest
  Altered sensorium
  Visual disturbances
  Local anesthetic systemic toxicity Adverse events of special interest classified as persistent referred to any condition (e.g., tingling, numbness, or sensory/motor weakness that affected the nerve block region, after the study drug administration) that persisted for >168 h from the time of onset.

A Serious Adverse Event (SAE) was defined as an AE or suspected adverse reaction that, in the view of either the Investigator or Sponsor, resulted in any of the following outcomes:
  Death: Any event that resulted in a subject's death was reported as an SAE. However, death, in and of itself, was not an AE; it was an outcome. The cause of death was the AE.
  Therefore, the Investigator was to make every effort to obtain and document the cause of death for all subjects who died during the study. If, despite all efforts, the cause of death remained unknown, the AE was to be documented as an "unspecified fatal event."
  Life-threatening: An AE was considered life-threatening if, in the view of either the Investigator or Sponsor, its occurrence placed the subject at immediate risk of death. It did not include an AE that, had it occurred in a more severe form, might have caused death.
  Inpatient hospitalization or prolongation of existing hospitalization: Hospitalization, in and of itself, did not represent an SAE. It was the AE leading to the subject's hospitalization that became "serious" when it required inpatient care. Consequently, an SAE was not to be reported in case of preplanned hospitalizations for a pre-existing condition that did not worsen during the study. However, any medical condition that delayed a subject's discharge from the hospital (i.e., prolonged hospitalization) or required the subject to be readmitted was reported as an SAE.
  Persistent or significant incapacity: A substantial disruption of a person's ability to conduct normal life functions.
  Congenital anomaly/birth defect: If suspected that exposure to the study drug prior to conception or during pregnancy may have resulted in an adverse outcome in the child.
  Medically significant: Important medical events that did not result in death, were not life-threatening, or did not require hospitalization, could be considered serious when, based upon appropriate medical judgment, they could jeopardize the subject and might have required medical or surgical intervention to prevent one of the outcomes listed in this definition.

Any SAE or death that occurred at any time after the subject signed the ICF through POD14, whether or not related to study drug, was to be reported within 24 h of discovery.

The invention claimed is:

1. A method of administering regional analgesia comprising a sciatic nerve block in the popliteal fossa of a patient, the method comprising:
  a) selecting an entry point of an injection needle in a leg of the patient;
  b) inserting the injection needle into the patient at the entry point;
  c) administering to a sciatic nerve sheath of the patient via the injection needle 133 mg of a pharmaceutical composition;
  wherein the pharmaceutical composition comprises multivesicular liposomes comprising:

at least one amphipathic lipid, at least one neutral lipid, and bupivacaine phosphate, wherein the bupivacaine phosphate is encapsulated within the multivesicular liposome, thereby administering the regional analgesia comprising the sciatic nerve block in the popliteal fossa of the patient.

2. The method of claim 1, wherein the injection needle is connected to a peripheral nerve stimulator (PNS).

3. The method of claim 2, wherein the PNS is used to identify the region where the sciatic nerve splits into the peroneal and tibial nerves.

4. The method of claim 1, wherein the injection needle is a 100 mm, 21-gauge needle.

5. The method of claim 1, wherein the insertion of the injection needle into the leg of the patient comprises piercing the perineural sheath.

6. The method of claim 1, wherein the entry point of the injection needle is in the lateral thigh.

7. The method of claim 1, wherein the method comprises administering about 30 mL of the pharmaceutical composition.

8. The method of claim 1, wherein the multivesicular liposomes comprise:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol,
  wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

9. The method of claim 1, further comprising administering to the patient a Mayo Field Block encircling the entire metatarsal bone.

10. A method of administering to a peroneal and a tibial nerve of a human patient a pharmaceutical composition for post-operative analgesia, the method comprising:
  a) selecting an entry point of an injection needle in a leg in a patient;
  b) advancing a needle tip of the injection needle within a region where the sciatic nerve splits into the peroneal and tibial nerves of the patient along a trajectory that extends between the entry point and where the sciatic nerve splits into the peroneal and tibial nerves;
  c) administering to said region through the injection needle 133 mg of a pharmaceutical composition;
  wherein the pharmaceutical composition comprises multivesicular liposomes comprising:
  at least one amphipathic lipid, at least one neutral lipid, and bupivacaine phosphate, wherein the bupivacaine phosphate is encapsulated within the multivesicular liposome,
    thereby administering to the peroneal and the tibial nerve of the human patient the pharmaceutical composition for post-operative analgesia.

11. The method of claim 10, wherein the injection needle is connected to a peripheral nerve stimulator (PNS).

12. The method of claim 11, wherein the PNS is used to identify the region where the sciatic nerve splits into the peroneal and tibial nerves.

13. The method of claim 11, wherein the injection needle is a 100 mm, 21-gauge needle.

14. The method of claim 11, wherein the entry point of the injection needle is in the lateral thigh.

15. The method of claim 10, wherein the method comprises administering about mL of the pharmaceutical composition.

16. The method of claim 10, wherein the multivesicular liposomes comprise:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol,
  wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

17. A method of administering postsurgical regional analgesia to a foot in a patient, the method comprising:
  a) selecting an entry point of an injection needle in a leg of the patient;
  b) inserting the injection needle into the leg of the patient at the entry point;
  c) administering to the patient 133 mg of a pharmaceutical composition within a sciatic nerve sheath;
  wherein the pharmaceutical composition comprises multivesicular liposomes comprising:
  at least one amphipathic lipid, at least one neutral lipid, and bupivacaine phosphate, wherein the bupivacaine phosphate is encapsulated within the multivesicular liposome,
    thereby administering postsurgical regional analgesia to a foot in the patient.

18. The method of claim 17, wherein a peripheral nerve stimulator (PNS) is used to identify the region where the sciatic nerve splits into the peroneal and tibial nerves.

19. The method of claim 17, wherein the injection needle is a 100 mm, 21-gauge needle.

20. The method of claim 17, wherein inserting the injection needle into the leg of the patient comprises advancing a needle tip of the injection needle within a region where the sciatic nerve splits into the peroneal and tibial nerves of the patient along a trajectory that extends between the entry point and the region where the sciatic nerve splits into the peroneal and tibial nerves.

21. The method of claim 17, wherein the insertion of the injection needle into the leg of the patient comprises piercing the perineural sheath.

22. The method of claim 17, wherein the method comprises administering about mL of the pharmaceutical composition.

23. The method of claim 17, wherein the multivesicular liposomes comprise:
- bupivacaine or a salt thereof;
- phosphoric acid;
- a lipid component comprising at least one amphipathic lipid and at least one neutral lipid lacking a hydrophilic head group; and,
- optionally, a cholesterol and/or a plant sterol,
- wherein said multivesicular liposomes are made by a process comprising:
  - a) preparing a first aqueous component comprising phosphoric acid;
  - b) preparing a lipid component comprising at least one organic solvent, at least one amphipathic lipid, and at least one neutral lipid lacking a hydrophilic head group;
  - c) mixing said first aqueous component and said lipid component to form a water-in-oil emulsion, wherein at least one component comprises bupivacaine or a salt thereof;
  - d) mixing said water-in-oil emulsion with a second aqueous component to form solvent spherules; and
  - e) removing the organic solvent from the solvent spherules to form multivesicular liposomes encapsulating bupivacaine phosphate.

24. The method of claim 17, further comprising administering to the patient a Mayo Field Block encircling the entire metatarsal bone.

25. A method of administering a sciatic nerve block in a popliteal fossa to reduce post-operative foot pain in a patient, the method comprising:
- a) selecting an entry point of an injection needle in a leg of the patient;
- b) advancing a needle tip of the injection needle within a region where the sciatic nerve splits into the peroneal and tibial nerves of the patient along a trajectory that extends between the entry point and the region where the sciatic nerve splits into the peroneal and tibial nerves;
- c) piercing with the needle tip of the injection needle the sciatic nerve sheath in said region;
- d) administering through the injection needle 133 mg of a multivesicular liposome pharmaceutical composition;
- wherein the multivesicular liposome pharmaceutical composition comprises:
- bupivacaine or a salt thereof;
- phosphoric acid;
- a lipid component comprising at least one amphipathic lipid and at least one neutral lipid lacking a hydrophilic head group; and,
- optionally, a cholesterol and/or a plant sterol,
- thereby administering a sciatic nerve block in the popliteal fossa to reduce post-operative foot pain in the patient.

26. The method of claim 25, wherein a peripheral nerve stimulator (PNS) is used to identify the region where the sciatic nerve splits into the peroneal and tibial nerves.

27. The method of claim 25, wherein the method comprises administering about mL of the pharmaceutical composition.

28. The method of claim 25, further comprising administering to the patient a Mayo Field Block encircling the entire metatarsal bone.

29. The method of claim 25, wherein the sciatic nerve is located by way of ultrasound guidance.

30. The method of claim 1, wherein inserting the injection needle into the leg of the patient comprises advancing a needle tip of the injection needle within a region where the sciatic nerve splits into the peroneal and tibial nerves of the patient along a trajectory that extends between the entry point and the region where the sciatic nerve splits into the peroneal and tibial nerves.

* * * * *

UNITED STATES PATENT AND TRADEMARK OFFICE
CERTIFICATE OF CORRECTION

| | | |
|---|---|---|
| PATENT NO. | : 11,918,565 B1 | Page 1 of 1 |
| APPLICATION NO. | : 18/104970 | |
| DATED | : March 5, 2024 | |
| INVENTOR(S) | : Roy Winston and Mary DiGiorgi | |

It is certified that error appears in the above-identified patent and that said Letters Patent is hereby corrected as shown below:

In the Claims

Column 24, Line 14, In Claim 15, delete "mL" and insert -- 30 mL --.

Column 25, Line 5, In Claim 22, delete "mL" and insert -- 30 mL --.

Column 26, Line 25 (approx.), In Claim 27, delete "mL" and insert -- 30 mL --.

Signed and Sealed this
Thirtieth Day of April, 2024

Katherine Kelly Vidal
*Director of the United States Patent and Trademark Office*